United States Patent
Lark, Jr.

(10) Patent No.: US 11,243,006 B2
(45) Date of Patent: Feb. 8, 2022

(54) INTELLIGENT LIGHTING CONTROL SYSTEM VIBRATION DETECTING FLOOR PUCK

(71) Applicant: Savant Systems, Inc., Hyannis, MA (US)

(72) Inventor: William Lark, Jr., Glendale, CA (US)

(73) Assignee: Savant Systems, Inc., Hyannis, MA (US)

( * ) Notice: Subject to any disclaimer, the term of this patent is extended or adjusted under 35 U.S.C. 154(b) by 0 days.

(21) Appl. No.: 16/758,962

(22) PCT Filed: Oct. 26, 2018

(86) PCT No.: PCT/US2018/057694
§ 371 (c)(1),
(2) Date: Apr. 24, 2020

(87) PCT Pub. No.: WO2019/084392
PCT Pub. Date: May 2, 2019

(65) Prior Publication Data
US 2020/0352001 A1    Nov. 5, 2020

Related U.S. Application Data

(60) Provisional application No. 62/577,294, filed on Oct. 26, 2017.

(51) Int. Cl.
*F24F 11/39*    (2018.01)
*H05B 47/115*    (2020.01)
(Continued)

(52) U.S. Cl.
CPC ............ *F24F 11/39* (2018.01); *A01K 15/021* (2013.01); *A01K 29/00* (2013.01); *A61B 5/11* (2013.01);
(Continued)

(58) Field of Classification Search
CPC .... H05B 47/105; H05B 47/115; H05B 47/11; H05B 47/19; H05B 47/16; H05B 47/14;
(Continued)

(56) References Cited

U.S. PATENT DOCUMENTS 6,406,308 B1    6/2002    Wang
2008/0094210 A1*    4/2008    Paradiso ............. H04L 12/2827
340/540

(Continued)

FOREIGN PATENT DOCUMENTS

WO    WO-2014/134637 A2    9/2014
WO    WO-2014134637 A2 *    9/2014    ............. H05B 47/19
(Continued)

OTHER PUBLICATIONS

PCT Notification of Transmittal of the International Search Report and the Written Opinion of the International Searching Authority, or the Declaration, International Searching Authority, International Application No. PCT/US 18/57694, dated Jan. 4, 2019, 21 pages.

*Primary Examiner* — Raymond R Chai
(74) *Attorney, Agent, or Firm* — Cesari and McKenna, LLP

(57) ABSTRACT

The present disclosure provides intelligent lighting control system configured for positioning on a floor surface and having a controller communicably coupled to a vibration sensor facing the floor and configured to detect movement in a room via the floor so as to control a flow of electricity received at an electrical wall outlet to a corded luminaire.

28 Claims, 18 Drawing Sheets

(51) Int. Cl.
  *H05B 47/11* (2020.01)
  *H05B 47/16* (2020.01)
  *A01K 29/00* (2006.01)
  *A61B 5/11* (2006.01)
  *A61B 5/00* (2006.01)
  *F21S 6/00* (2006.01)
  *G01H 17/00* (2006.01)
  *G01N 33/00* (2006.01)
  *G01P 13/00* (2006.01)
  *G01S 13/89* (2006.01)
  *G08B 21/02* (2006.01)
  *G08B 21/18* (2006.01)
  *A01K 15/02* (2006.01)
  *G08B 21/14* (2006.01)
  *H05B 45/00* (2020.01)
  *H05B 47/12* (2020.01)
  *H05B 47/14* (2020.01)
  *H05B 47/175* (2020.01)

(52) U.S. Cl.
  CPC ............ *A61B 5/4806* (2013.01); *F21S 6/004* (2013.01); *G01H 17/00* (2013.01); *G01N 33/0004* (2013.01); *G01P 13/00* (2013.01); *G01S 13/89* (2013.01); *G08B 21/02* (2013.01); *G08B 21/14* (2013.01); *G08B 21/18* (2013.01); *G08B 21/182* (2013.01); *H05B 45/00* (2020.01); *H05B 47/11* (2020.01); *H05B 47/115* (2020.01); *H05B 47/12* (2020.01); *H05B 47/14* (2020.01); *H05B 47/16* (2020.01); *H05B 47/175* (2020.01); *A61B 2562/0204* (2013.01)

(58) Field of Classification Search
  CPC ...... H05B 47/12; H05B 47/175; H05B 45/00; G08B 21/182; G08B 21/14; G08B 21/02; G08B 21/18; A01K 15/021; A01K 29/00; F24F 11/39; A61B 11/4806; A61B 2562/0204; F21S 6/004; G01H 17/00; G01N 33/0004; G01P 13/00; G01S 13/89; Y02B 20/40
  See application file for complete search history.

(56) References Cited

U.S. PATENT DOCUMENTS

| | | | | |
|---|---|---|---|---|
| 2008/0284350 | A1* | 11/2008 | Xu | H05B 41/36 315/291 |
| 2010/0294915 | A1* | 11/2010 | Williams | G01J 5/0896 250/206.1 |
| 2011/0121654 | A1 | 5/2011 | Recker et al. | |
| 2013/0234625 | A1* | 9/2013 | Kondo | H05B 47/115 315/313 |
| 2014/0107846 | A1* | 4/2014 | Li | F24F 11/30 700/275 |
| 2016/0224064 | A1 | 8/2016 | Fleisig | |
| 2017/0238401 | A1 | 8/2017 | Sadwick et al. | |
| 2017/0295624 | A1 | 10/2017 | Lark, Jr. et al. | |

FOREIGN PATENT DOCUMENTS

| | | | | |
|---|---|---|---|---|
| WO | WO-2015/054225 | A1 | 4/2015 | |
| WO | WO-2015054225 | A1 * | 4/2015 | ............ G08B 21/12 |
| WO | WO-2017/140617 | A1 | 8/2017 | |
| WO | WO-2017140617 | A1 * | 8/2017 | ........... H05B 47/105 |

* cited by examiner

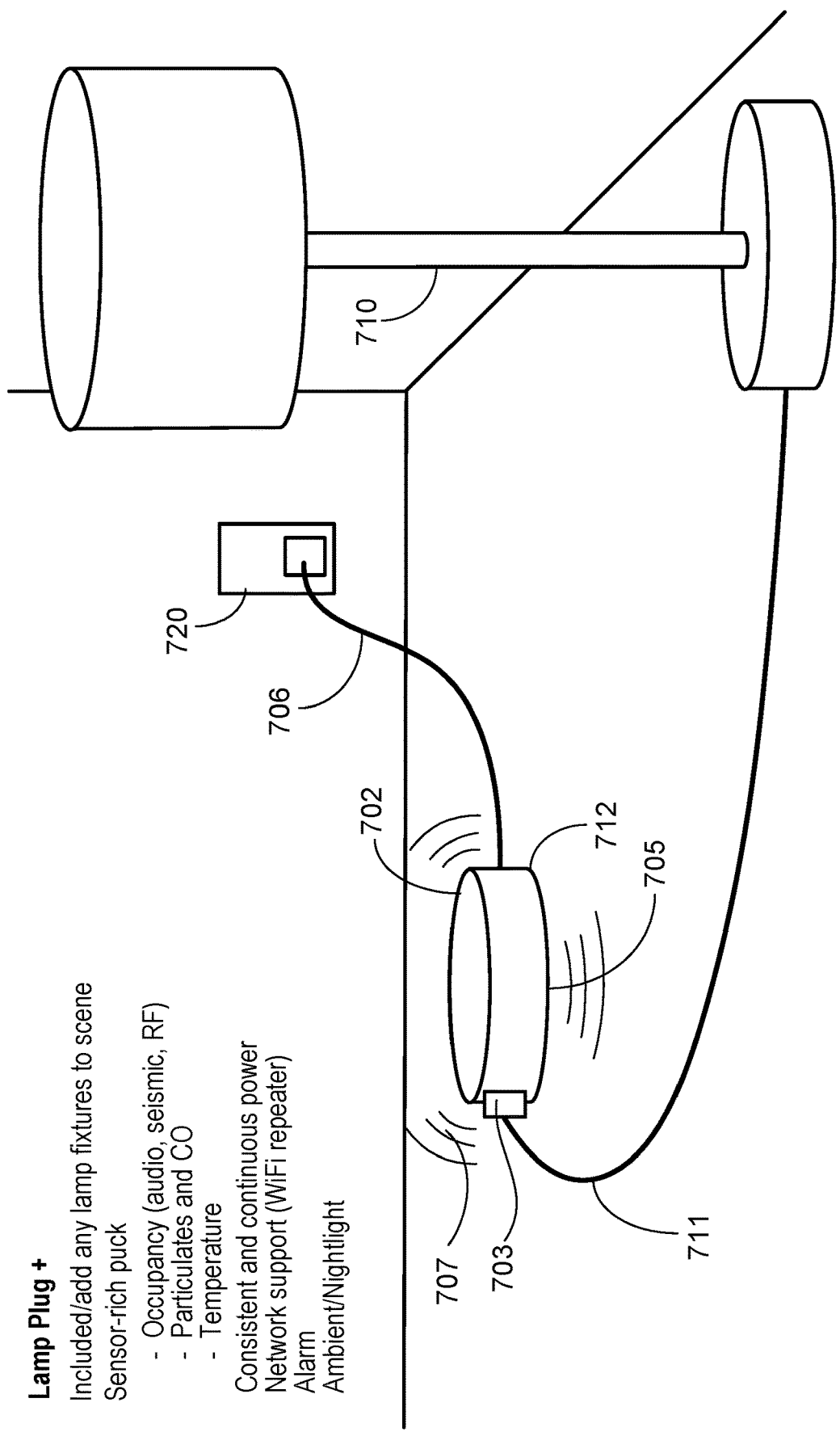

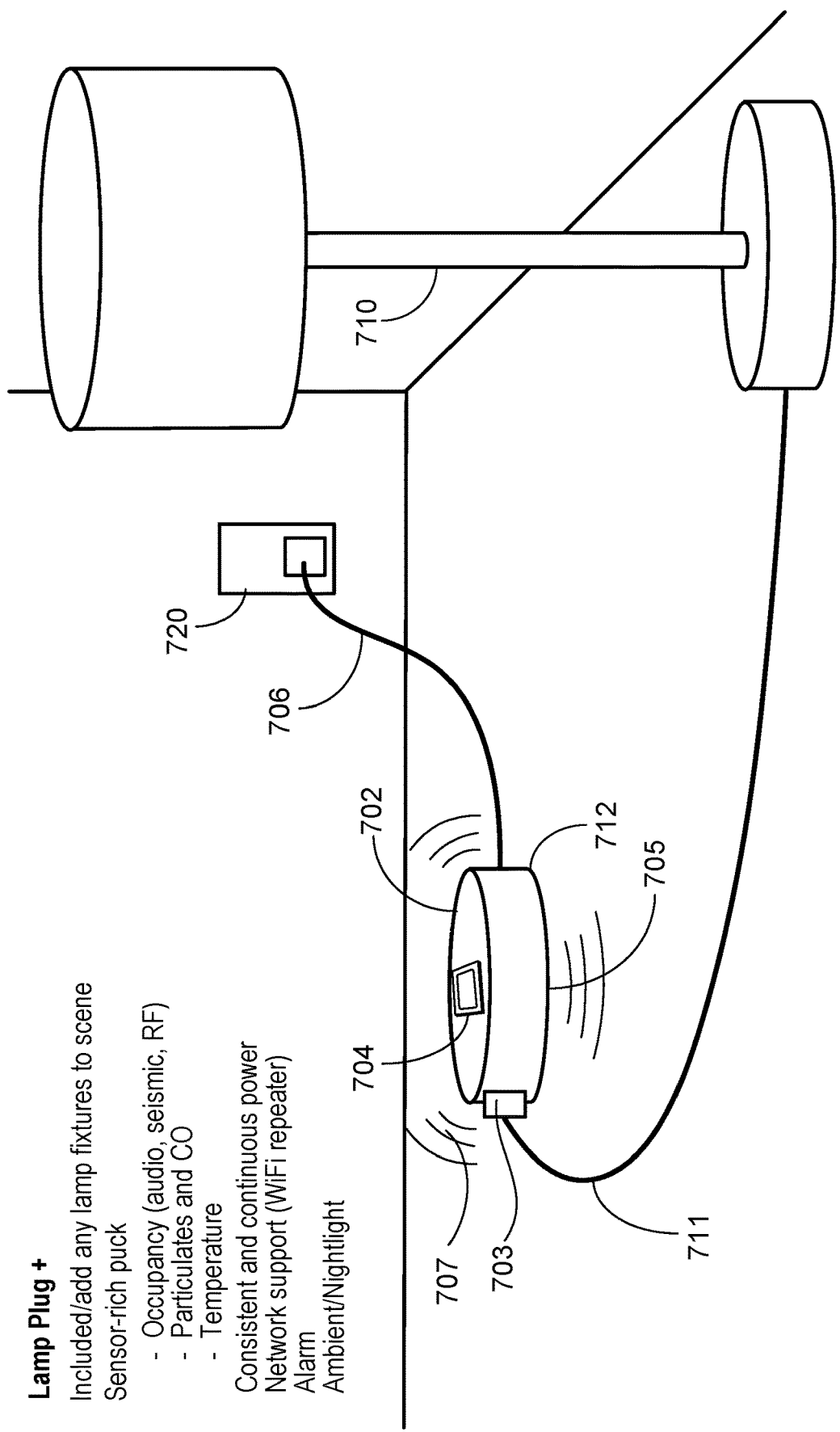

INTELLIGENT LIGHTING CONTROL SYSTEM VIBRATION DETECTING FLOOR PUCK

RELATED APPLICATION

The present application is a National Stage of International Application No. PCT/US2018/057694, filed Oct. 26, 2017, entitled INTELLIGENT LIGHTING CONTROL SYSTEM FLOOR PUCK APPARATUSES, SYSTEMS, AND METHODS, which application claims priority to commonly owned U.S. Provisional Patent Application No. 62/577,294, filed on Oct. 26, 2017, entitled INTELLIGENT LIGHTING CONTROL SYSTEM FLOOR PUCK APPARATUSES, SYSTEMS, AND METHODS, which applications are incorporated herein by reference in their entirety.

TECHNICAL FIELD

The present application relates generally to the field of lighting control systems.

BACKGROUND

Customizing and automating home lighting control devices is often epitomized by the installation of unsightly lighting switches that are inundated with light switches confusingly mapped to respective fixtures. Automated home lighting control systems can also include large, complex, expensive central hubs that require expert or skilled technicians for installation and/or operation. Smart light bulbs and/or Wi-Fi enabled lightbulbs introduced into any of these contexts or even in simpler ones can disadvantageously be limited by the light switch that it is associated with and/or the lighting fixture itself. For example, if a light switch associated with a smart light bulb is switched off the smart light bulb becomes inoperable.

As the components and connections of lighting control devices expands implementing changes to the system and controlling operation of the system can also change.

SUMMARY

The inventors have appreciated that various embodiments disclosed herein provide apparatuses, systems, and methods for detecting activities and conditions to intelligently control lighting control systems.

Various embodiments provide lighting control systems. The lighting control systems include a base housing. The lighting control systems include a base electrical plug extending from the base housing and configured for plugging into a wall electrical outlet. The lighting control systems include a base electrical outlet in the base housing configured for electrically coupling the lighting control system with a corded luminaire via a luminaire electrical plug. The lighting control systems include at least one sensor system coupled to the base housing. The lighting control systems include a controller communicably coupled to the at least one sensor. The controller is configured to control a flow of electricity received through the base electrical plug from the electrical wall outlet and flowing, at least in part, to the corded luminaire via the luminaire electrical plug. The controller is configured to control the flow of electricity to the corded luminaire based on an input detected by the at least one sensor, whereby a light emitting element in the free standing corded luminaire can be turned on, turned off, dimmed, or have the color temperature changed.

In some implementations, the base housing is configured for positioning on a floor surface.

In some implementations, the at least one sensor comprises at least one sensor positioned on a bottom surface of the base housing.

In some implementations, the at least one sensor comprises at least one sensor positioned on a top surface of the base housing.

In some implementations, the corded luminaire comprises a free standing corded luminaire.

In some implementations, the the at least one sensor comprises at least one of a vibration sensor, a sonar sensor, a low-pass microphone, a RF sensor, a radar, a CO2 sensor, a humidity sensor, and a thermometer.

In some implementations, the vibration sensor is facing a downward direction.

In some implementations, the electrical outlet is positioned in a peripheral portion of the housing.

In some implementations, the controller is configured to determine a floor type from a detection of the at least one sensor.

In some implementations, the base housing is disk shaped.

In some implementations, the controller is configured to auto-tune a strength of the at least one sensor dependent upon a proximity of the lighting control system to one or more pieces of surrounding furniture and walls detected via an ultrasonic and/or time-of-flight sensor.

In some implementations, the controller is configured to auto-tune a strength of a wireless antenna dependent upon proximity to surrounding occluding furniture and walls via use of ultrasonic and/or time-of-flight sensors.

In some implementations, the controller is configured to map out a home's floor plan when multiple lighting control systems are used in unison (1) for a call and response to determine relative distances and/or angles between them, (2) to determine relative distances by RSSI measurements between lighting control modules, (3) as radar sensors (4) as ultra-sonic speakers and microphones to triangulate distances from one or more walls and each other.

In some implementations, the controller is configured to analyze temperature differentials, thermal deficiencies, and environment profile throughout a home with the use of D-thermometers and humidity sensors within a plurality of lighting control systems positioned throughout the home.

In some implementations, the controller is configured to monitor a sleep pattern via a motion sensor and/or microphone.

In some implementations, the controller is configured to analyze changes in occupancy via changes in CO2 readings obtained by the at least one sensor.

In some implementations, the controller is configured to monitor air quality by measuring particulates and CO levels and at least one of communicate one or more countermeasures wirelessly to HVAC system, notify a user [to change an air filter], or send a notification to a mobile electronic device and activate an alarm system.

In some implementations, the controller is configured to communicate to other lighting control systems via low-frequency audio through one or more floors and walls in a home.

In some implementations, the controller is configured to detect a bulb type of a bulb connected to the corded luminaire via at least one of a current sensor and voltage sensor used to analyze a power line.

In some implementations, the controller is configured to turn on the corded luminaire to provide a nightlight in response to sensing vibration.

In some implementations, the controller is configured to turn on the corded luminaire to provide a nightlight in response to sensing vibration and detecting that a room is dark.

In some implementations, the the controller is configured to adjust an intensity of the nightlight in response to changes in the strength of the sensed vibrations.

In some implementations, the the controller is configured to analyze vibration sensed by the at least one sensor concurrently with activating the corded luminaire as an alarm to wake up.

In some implementations, the controller is configured to only deactivate the alarm once the at least one sensor senses that an occupant has stood up and/or begun walking via the at least one sensor and/or a floor motion sensor.

In some implementations, the controller is configured to monitor pet motion and track behavior throughout a day via various sensors in 360-degrees of direction.

In some implementations, the at least one sensor comprises one or more of: a passive infrared sensor, an ultrasonic sensor, a time-of-flight sensor, a motion/seismic sensor, and a microphone.

In some implementations, the lighting control system is implemented to monitor child movement and deter via an alarm or an alert when a detected child is determined to be in close proximity to an pre-identified dangerous area.

In some implementations, the controller is configured to guide pets toward or away from areas of the home via utilization of high-frequency audio.

In some implementations, the the high frequency audio is implemented in harmony (sound varies in harmony from loudest in spaces to deter to quiet/off in destination) via a plurality of lighting control systems.

In some implementations, the controller is configured to utilize current and voltage sensing to determine what is plugged into the lighting control system and to regulate power based on the determination to prevent damage.

In some implementations, the housing includes a movable outlet cover.

In some implementations, the base housing comprises a well including a first electrical connector positioned in the well and a light switch module configured for nesting, at least in part, in the well. The light switch module includes a module housing, a graphical user interface coupled to the module housing, a power storage system housed in the module housing, and a second electrical connector electrically connected to the power storage system. The second electrical connector is configured for engagement with and electrical coupling to the first electrical connector of the base module when nested in the well of the base housing.

In some implementations, the controller is positioned in the module housing nested in the well of the base housing.

In some implementations, the base housing comprises a well comprising a high power circuit electrical connector for sinking and sourcing high in-line power from and to the wall electrical outlet, the high power circuit electrical connector configured to engage a low power circuit electrical connector of a light switch module configured to nest, at least in part, in the well, the light switch module comprising an actuator circuit board system comprising a low power circuit electrically connected to a low power circuit electrical connector, the low power circuit comprising at least one processor.

In some implementations, the light switch module further comprises at least one sensor.

Various embodiments provide methods of operating a lighting control system according to according to one or more of the preceding embodiments and implementations.

Various embodiments provide a lighting control system apparatus for automated lighting adjustment, the apparatus comprising a lighting control system configured to operate according to according to one or more of the preceding embodiments and implementations.

It should be appreciated that all combinations of the foregoing concepts and additional concepts discussed in greater detail below (provided such concepts are not mutually inconsistent) are contemplated as being part of the inventive subject matter disclosed herein. In particular, all combinations of claimed subject matter appearing at the end of this disclosure are contemplated as being part of the inventive subject matter disclosed herein. It should also be appreciated that terminology explicitly employed herein that also may appear in any disclosure incorporated by reference should be accorded a meaning most consistent with the particular concepts disclosed herein.

BRIEF DESCRIPTION OF THE DRAWINGS

The drawings primarily are for illustrative purposes and are not intended to limit the scope of the inventive subject matter described herein. The drawings are not necessarily to scale; in some instances, various aspects of the inventive subject matter disclosed herein may be shown exaggerated or enlarged in the drawings to facilitate an understanding of different features. In the drawings, like reference characters generally refer to like features (e.g., functionally similar and/or structurally similar elements).

FIGS. 7A and 7B are schematics of light control systems.

The features and advantages of the inventive subject matter disclosed herein will become more apparent from the detailed description set forth below when taken in conjunction with the drawings.

DETAILED DESCRIPTION

Following below are more detailed descriptions of various concepts related to, and exemplary embodiments of, inventive systems, methods and components of lighting control devices.

Figure 1A:
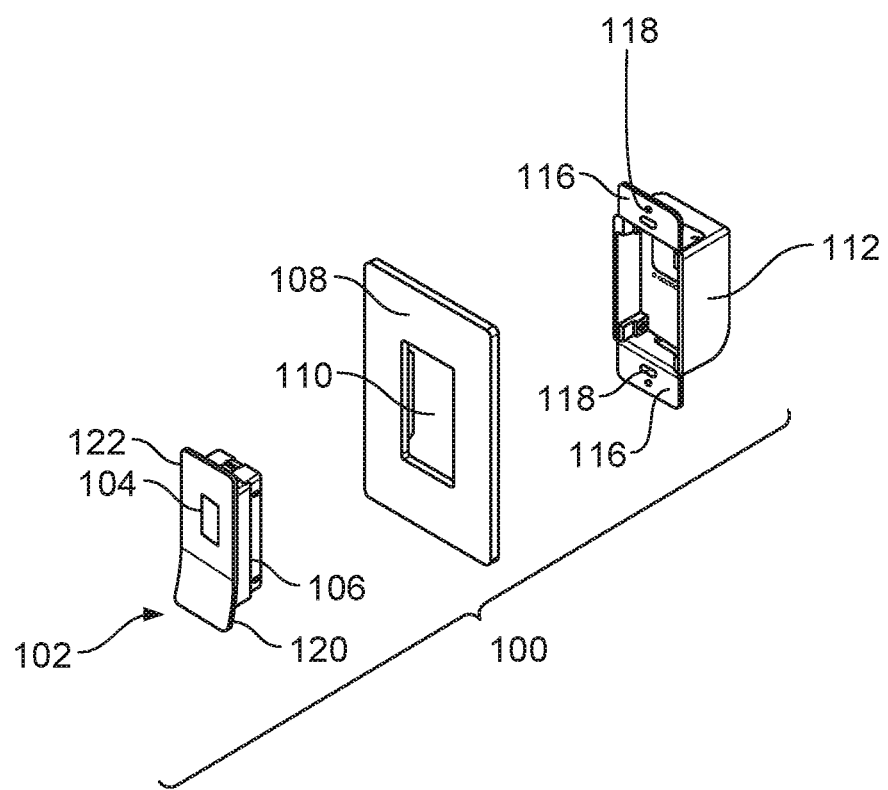
FIG. 1A is a perspective partially exploded view of a lighting control device.

FIG. 1A is a perspective partially exploded view of a lighting control device 100. The lighting control device 100 includes a switch module 102 including a light switch actuator 106 and a tactile display 104 housed in the light switch actuator 106. The lighting control device 100 also includes a wall plate cover 108 including a switch module opening 110 extending therethrough. The lighting control device 100 also includes a base module 112 configured for coupling to the switch module 102 via multi-pin socket 114. The base module 112 is sized and configured for receipt within a one-gang wall electrical box and has a volume corresponding substantially thereto. The base module 112 is configured to be coupled to a wall electrical box via connection tabs 116 and fastener apertures 118 in the connection tabs 116.

The light switch actuator 106 includes an outer actuation surface 122, which as discussed further herein may be composed of glass. The actuation surface 122 is movable, for example, by pushing on the curved foot 120 to cause the light switch actuator 106 to pivot, for example. The pivoting of the light switch actuator 106 and the actuation surface 122 causes a contact component (shown in FIG. 2) of the switch actuator 106 to move from a first position to a second position. Movement of the contact component causes a connection of an electrical flow path, for example by allowing two electrical contacts to connect or by connecting the contact component with an electrical contact. The connecting of the electrical flow path, permits electrical energy supplied by a power source connected to the base module 112 to energize or activate the tactile display 104, as discussed in further detail herein. The tactile display 104 is structured in the switch module to move contemporaneously with at least a portion of the actuation surface 122 and with the actuator 106. When activated or energized, the tactile display 104 allows a user to define or select predefined lighting settings where the lighting settings change the voltage or power supplied to one or more light fixtures. The change in power supplied to the light fixtures may include a plurality of different voltages supplied to each fixture and may be based on various parameters including, but not limited to, location, light intensity, light color, type of bulb, type of light, ambient light levels, time of day, kind of activity, room temperature, noise level, energy costs, user proximity, user identity, or various other parameters which may be specified or detected. Furthermore, the lighting control device 100 may be connected to all of the lights in a room or even in a house and can be configured to operate cooperatively with one or more other lighting control devices 100 located in a unit or room and connected to the same or distinct lighting fixtures.

Figure 1B:
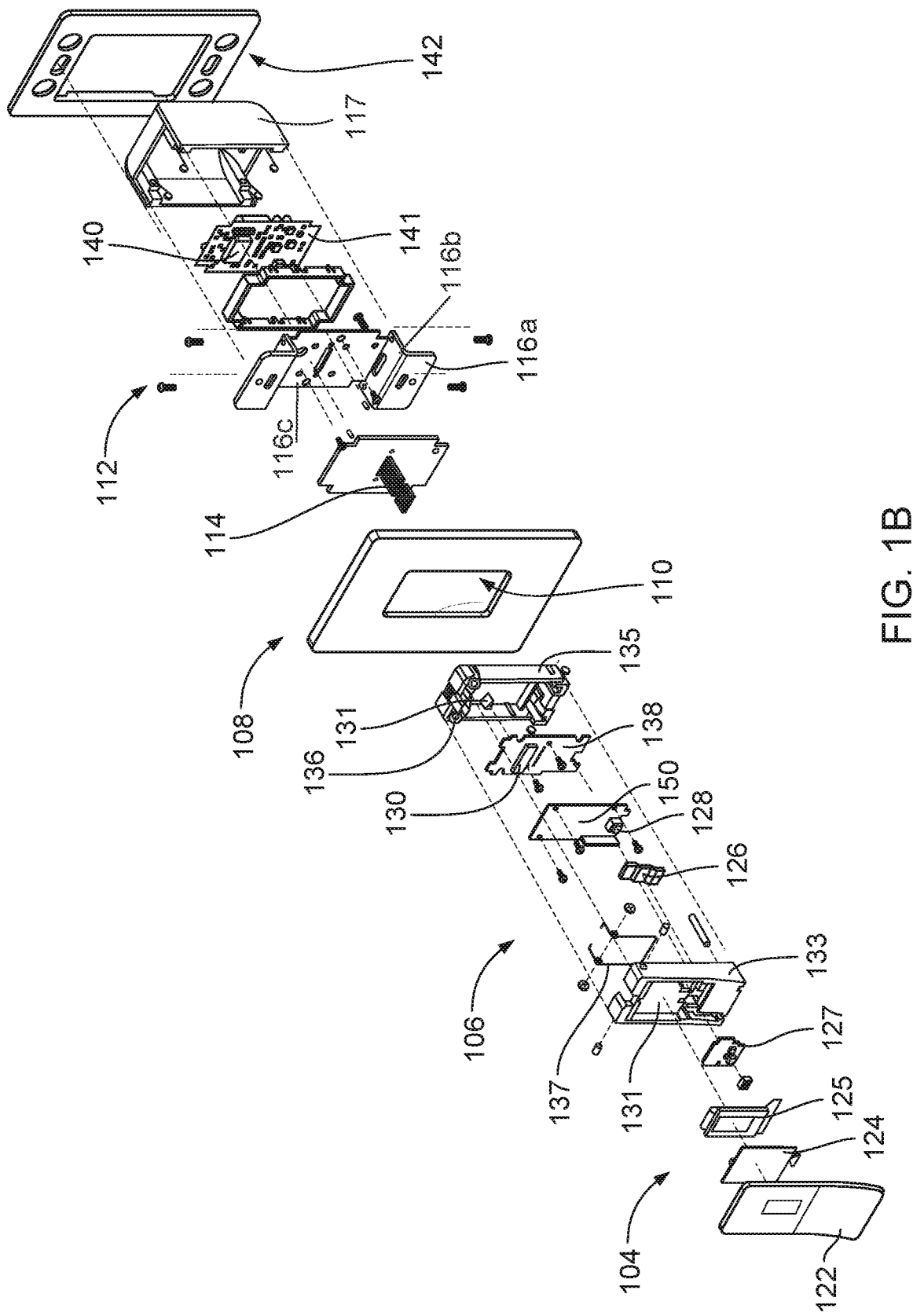
FIG. 1B is a fully exploded view of the lighting control device of FIG. 1A

FIG. 1B is a fully exploded view of the lighting control device 100 of FIG. 1A. As demonstrated in FIG. 1B, the tactile display 104 is positioned between the outer actuation surface 122 and the light switch actuator 106. The actuation surface 122 may be composed of an impact-resistant glass material permitting light from the tactile display 104 and/or a clear sight of path for sensors 127 or other lights, such as a light from light pipe 126 indicating activation to pass through the actuation surface 122. The tactile display 104 is composed of a polymer-based capacitive touch layer 124 and a light emitting diode panel 125, which are controlled via one or more modules or processors positioned on the printed circuit board 129. The tactile display 104 is housed within a recess 131 of the light switch actuator 106 beneath the actuation surface 122. The light switch actuator 106 may be formed as a thermoplastic housing including a housing cover 133 and a housing base 135. The light switch actuator housing cover 133 is pivotally connected to the housing base 135 via pins 136 and the housing cover 133 is biased with respect the housing base 135 via torsion spring 137. In particular embodiments, the light switch actuator housing cover 133 may be configured to slide or otherwise translate or rotate. The outer actuation surface 122 is biased with the switch actuator housing cover 133 and moves contemporaneously therewith in concert with the tactile display 104 housed in the cover component 133 of the light switch actuator 106. The light switch actuator 106 includes a switch pin 128 movable between positions to close an open circuit on the primary printed circuit board substrate 150, which board also houses a switch controller or processor. In certain embodiments the light switch actuator 106 may include a circuit board stack, including the primary printed circuit board substrate 150 and a secondary printed circuit board 138. The light switch actuator 106 may include a latch 136 for coupling to the base module 112 (e.g. as the light switch actuator 106 is passed through the opening 110 in the wall plate cover 108), which latch causes the light switch actuator 106 to click into place. The housing base 135 includes a multi-pin connector or plug 134 configured to engage the multi-pin socket 114 of the base module 112.

The lighting control device 100 includes a mounting chassis 142 configured to be installed to an electrical wall box. The mounting chassis 142 creates an even surface for installation of the other modules (e.g., the base module 112 and the switch module 102). Once the base module is connected to the electrical wall box via the mounting chassis 142, the wall plate cover 108 can be coupled to the mounting chassis 142 and the light switch actuator 106 can be inserted through the switch module opening 110. In particular embodiments, the wall plate cover can be coupled to the mounting chassis 142 and/or the tabs 116 of the base module via magnets. The magnets may be recessed within openings of a portion of the wall plate cover 108. As noted, the base module 112 is configured to be coupled to the mounting chassis 142 via connection tabs 116. The base module 112 is further configured to be electrically coupled to a power source (e.g., an electrical wire coming from an electrical breaker box to the electrical wall box) and to one or more light fixtures wired to the electrical box. Accordingly, the base module 112 provides an interface between a power source, the light switch actuator 106, and one or more light fixtures. The base module includes a processor 140 and a circuit board 141 for managing the power supplied by the power source and routed to the one or more light fixtures in accordance with a light setting selection identified via the light switch actuator 106 or the tactile display 104.

One or more of the processor on the printed circuit board 138a or 138b 130 and the base module processor 140 may include wireless links for communication with one or more remote electronic device such as a mobile phone, a tablet, a laptop, another mobile computing devices, one or more other lighting control devices 100 or other electronic devices operating in a location. In certain implementations the wireless links permit communication with one or more devices including, but not limited to smart light bulbs, thermostats, garage door openers, door locks, remote controls, televisions, security systems, security cameras, smoke detectors, video game consoles, robotic systems, or other communication enabled sensing and/or actuation devices or appliances. The wireless links may include BLUETOOTH classes, Wi-Fi, Bluetooth-low-energy, also known as BLE (BLE and BT classic are completely different protocols that just share the branding), 802.15.4, Worldwide Interoperability for Microwave Access (WiMAX), an infrared channel or satellite band. The wireless links may also include any cellular network standards used to communicate among mobile devices, including, but not limited to, standards that qualify as 1G, 2G, 3G, or 4G. The network standards may qualify as one or more generation of mobile telecommunication standards by fulfilling a specification or standards such as the specifications maintained by International Telecommunication Union. The 3G standards, for example, may correspond to the International Mobile Telecommunications-2000 (IMT-2000) specification, and the 4G standards may correspond to the International Mobile Telecommunications Advanced (IMT-Advanced) specification. Examples of cellular network standards include AMPS, GSM, GPRS, UMTS, LTE, LTE Advanced, Mobile WiMAX, and WiMAX-Advanced. Cellular network standards may use various channel access methods e.g. FDMA, TDMA, CDMA, or SDMA. In some embodiments, different types of data may be transmitted via different links and standards. In other embodiments, the same types of data may be transmitted via different links and standards.

Figure 2A:
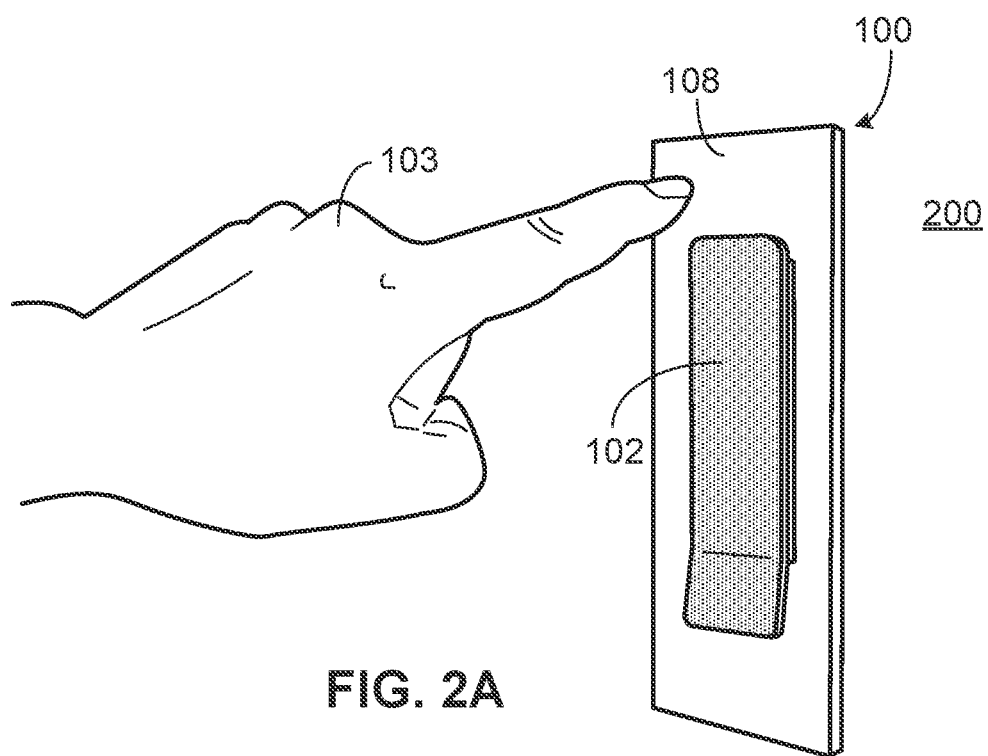
FIG. 2A shows the lighting control device of FIG. 1A mounted on a wall.

FIG. 2A shows the lighting control device 100 of FIG. 1A mounted on a wall 200. As demonstrated in FIG. 2A, the base module 112 is not visible upon installation of the lighting control device 100 in view of the wall plate cover 108. Because the wall plate cover 108 attaches to the base module 112, the wall plate cover 108 appears to be floating on the wall 200. The lighting control device 100 may be activated by a user 103 interacting with the outer actuation surface 122 and the tactile display 104.

Figure 2B:
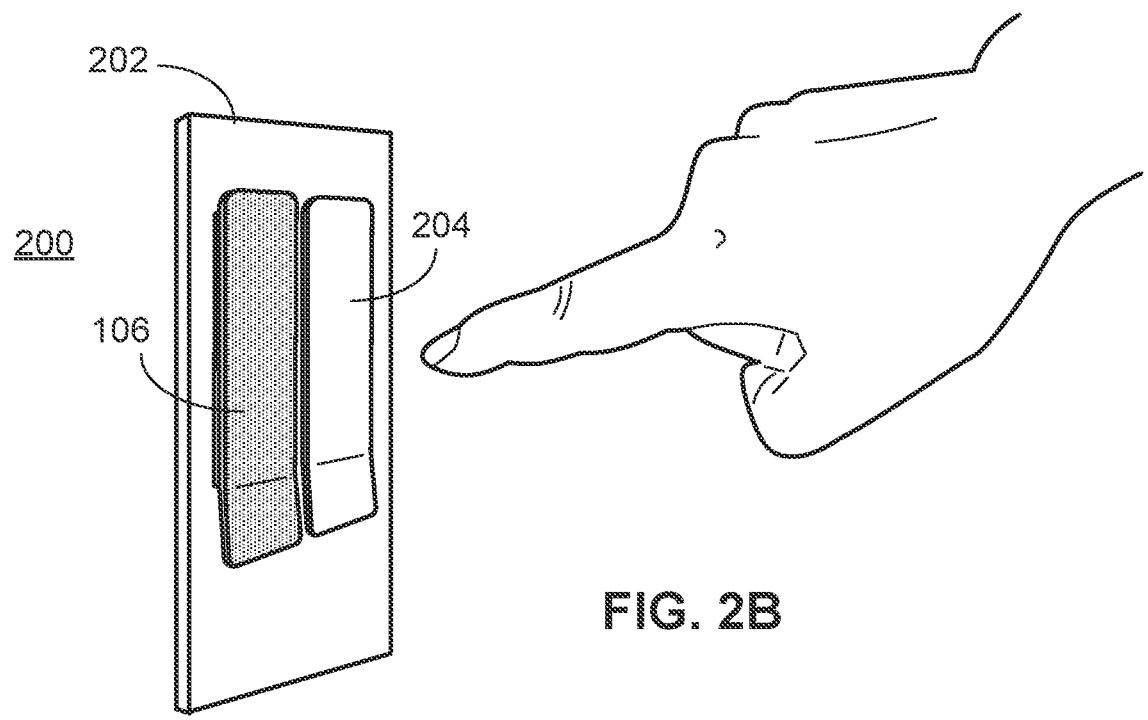
FIGS. 2B and 2C illustrate multi-switch lighting control devices.
Figure 2C:
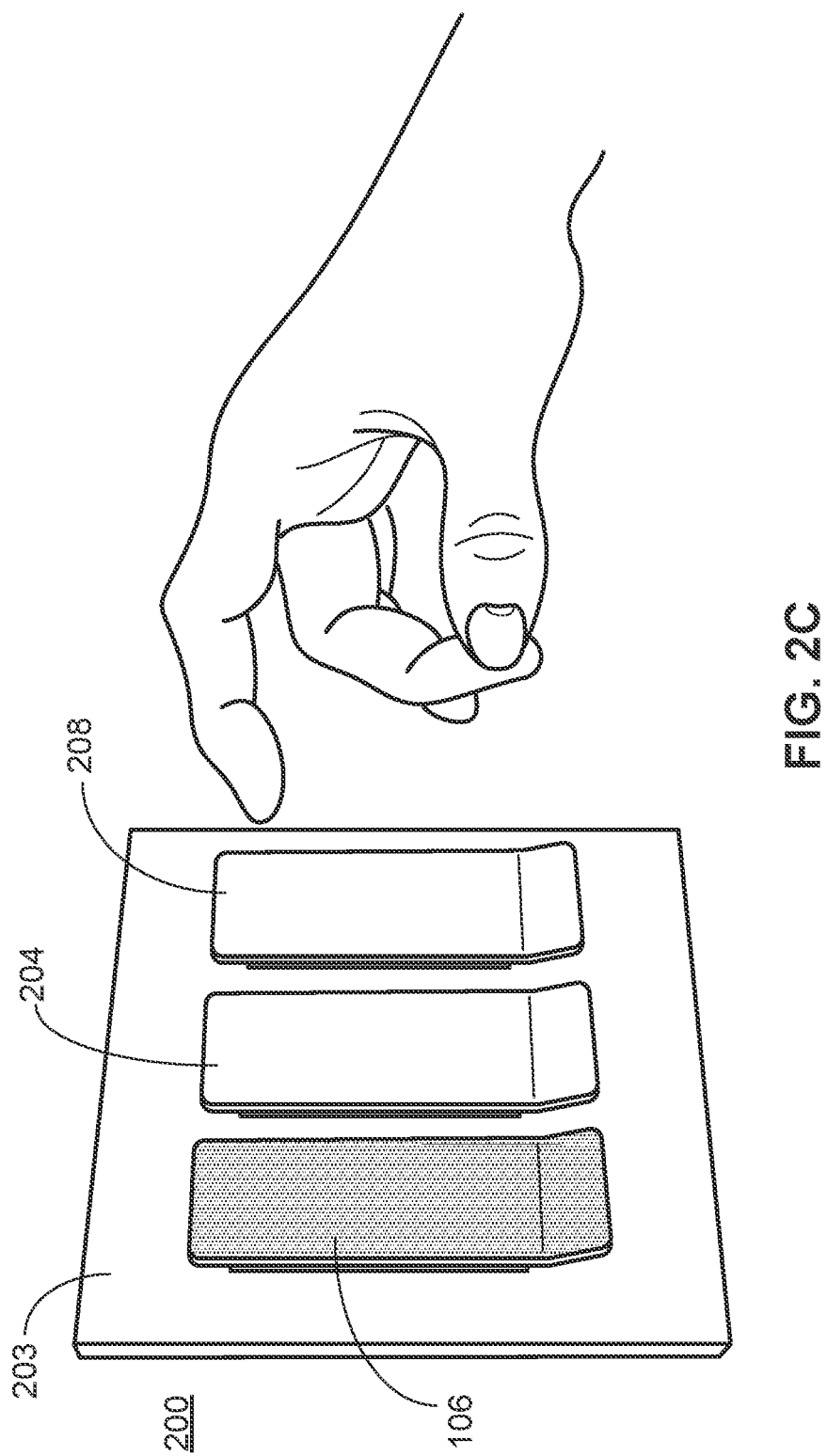

FIGS. 2B and 2C illustrate multi-switch configurations of multiple lighting control device. FIGS. 2B and 2C illustrate a two switch and three switch embodiment respectively where the lighting control devices 202 and 203 each include a light switch actuator 106 as well as auxiliary switches 204 and 208, as well as 2 and 3 base modules 112, respectively.

FIGS. 3A-3F illustrate a lighting control device transitioning through various lighting settings and a room having lighting fixtures controlled by the lighting control device.

Figure 3A:
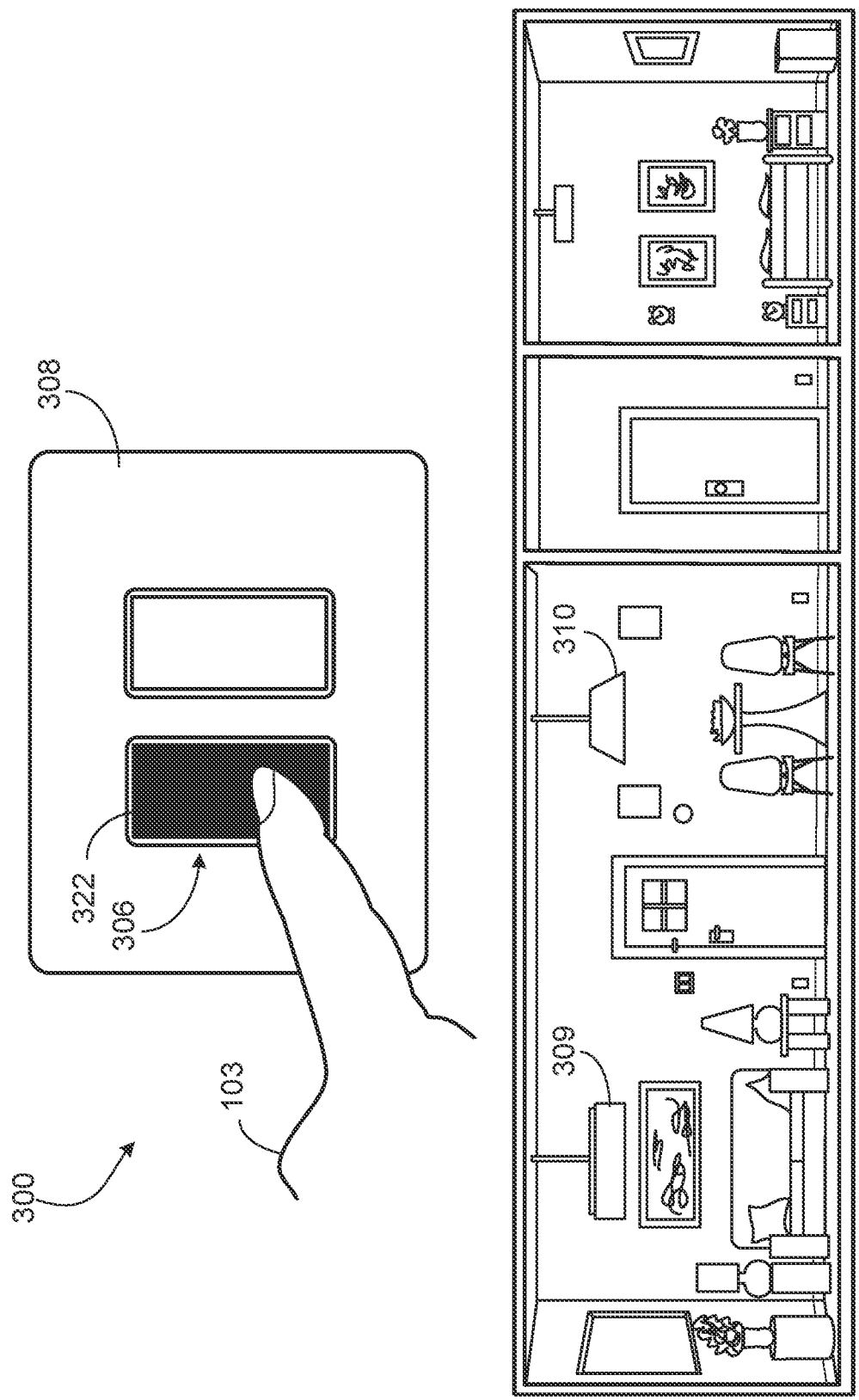
FIGS. 3A-3F illustrate a lighting control device transitioning through various lighting settings and a room having lighting fixtures controlled by the lighting control device.
Figure 3B:
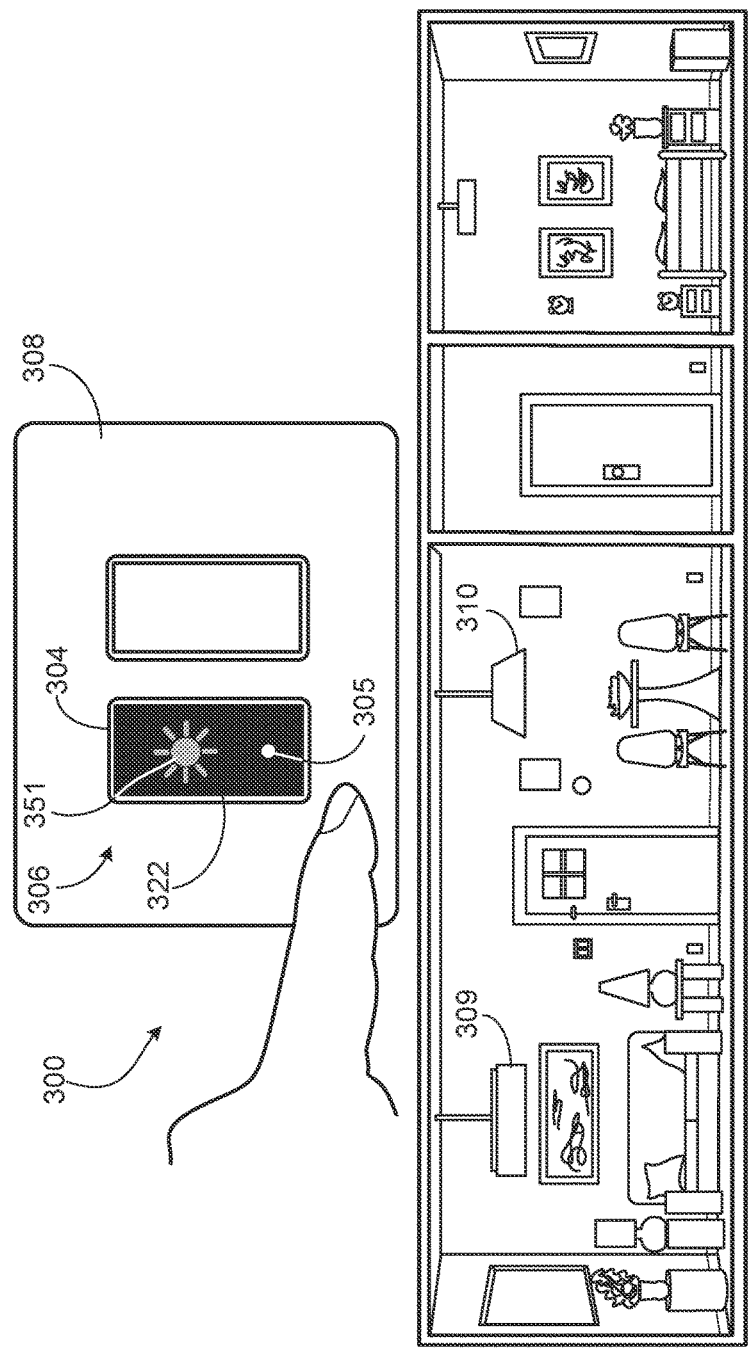
Figure 3C:
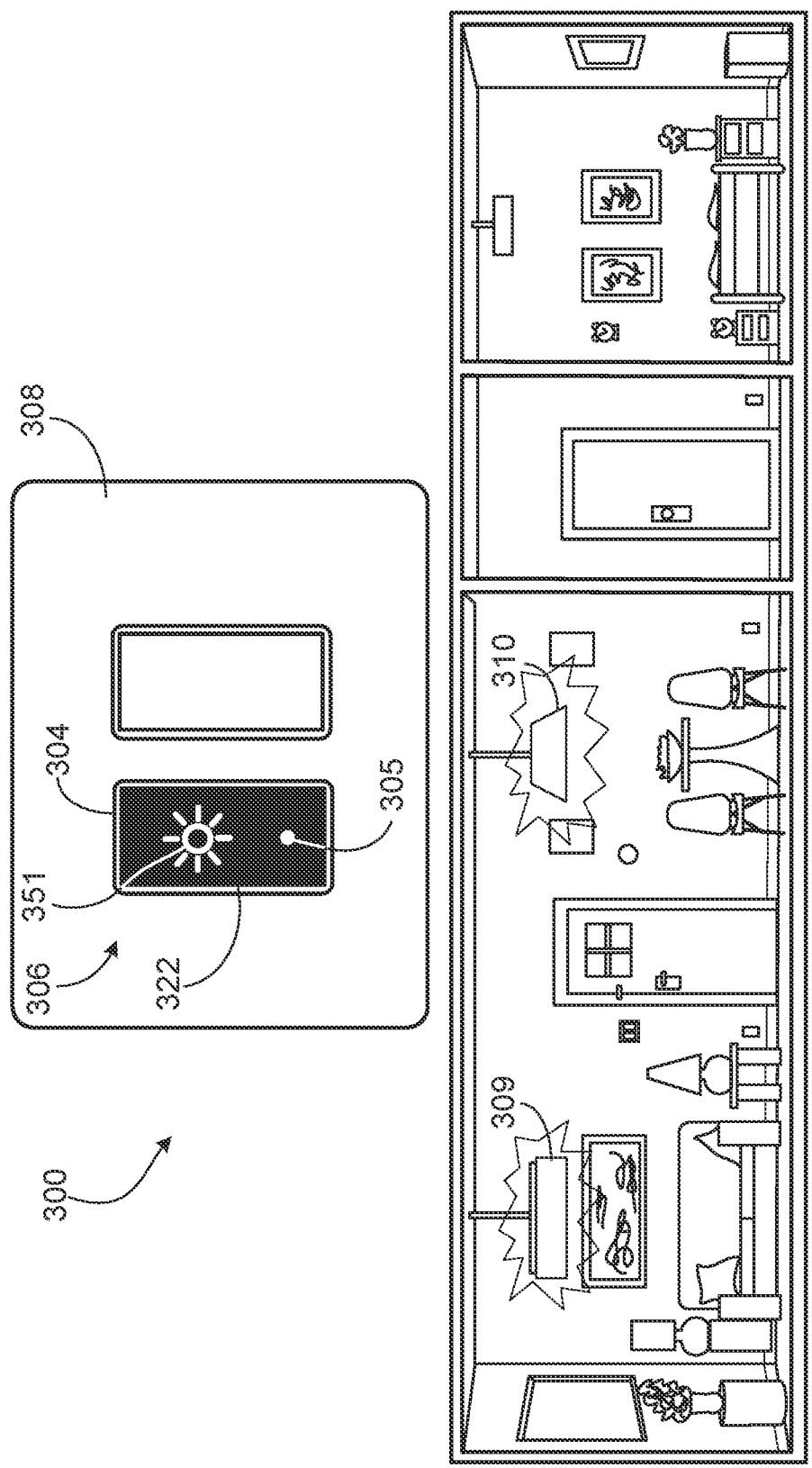
Figure 3D:
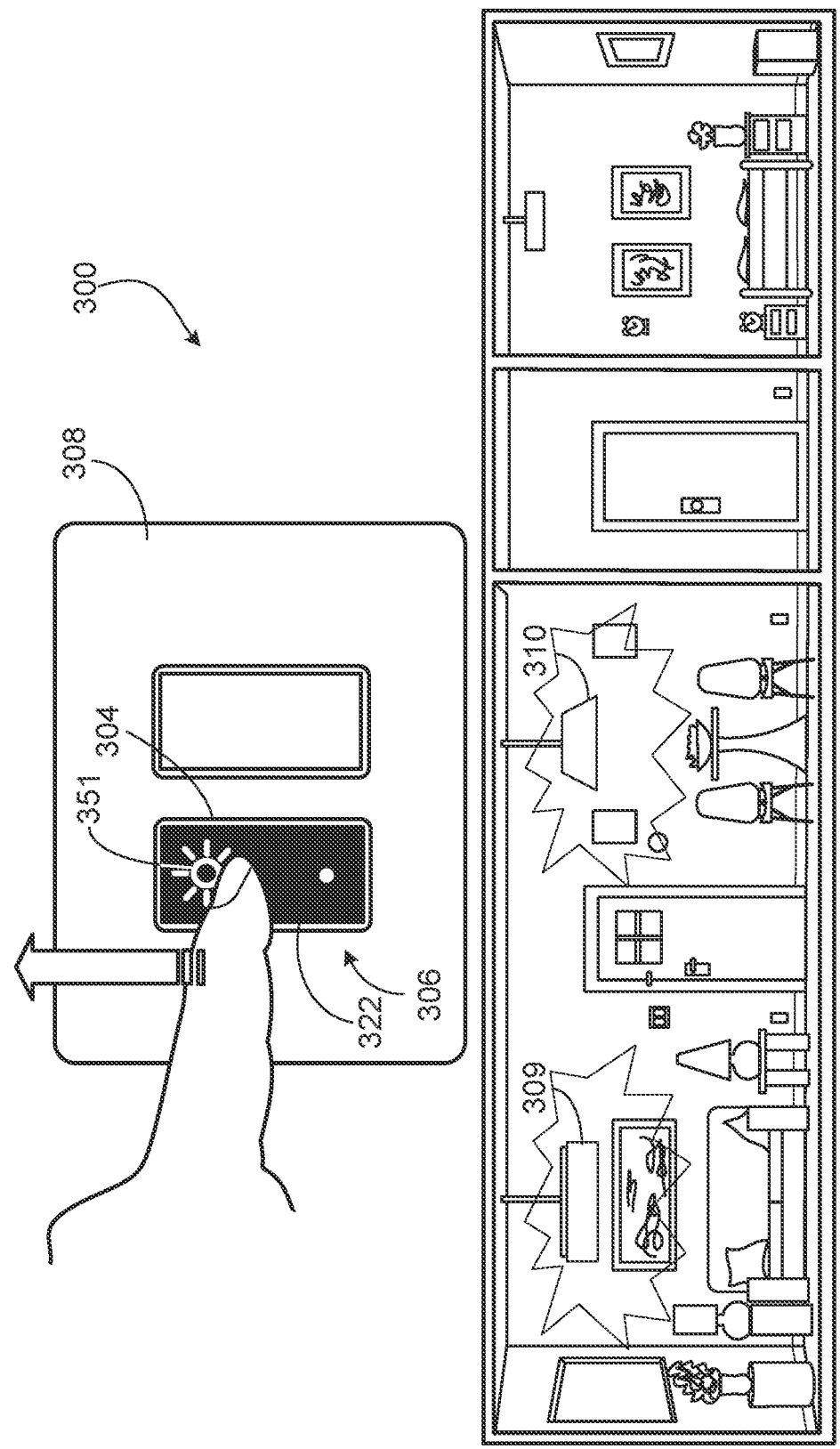
Figure 3E:
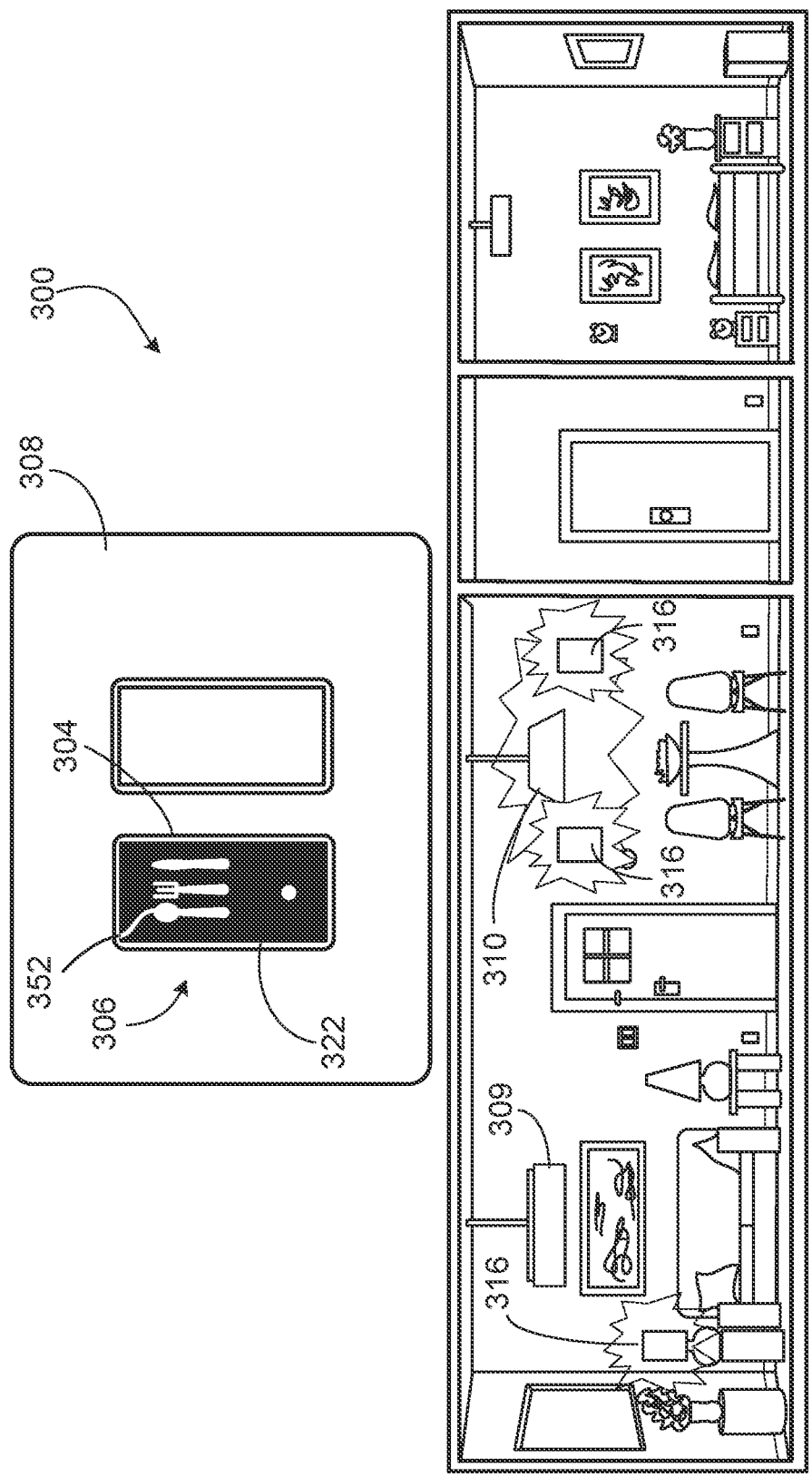
Figure 3F:
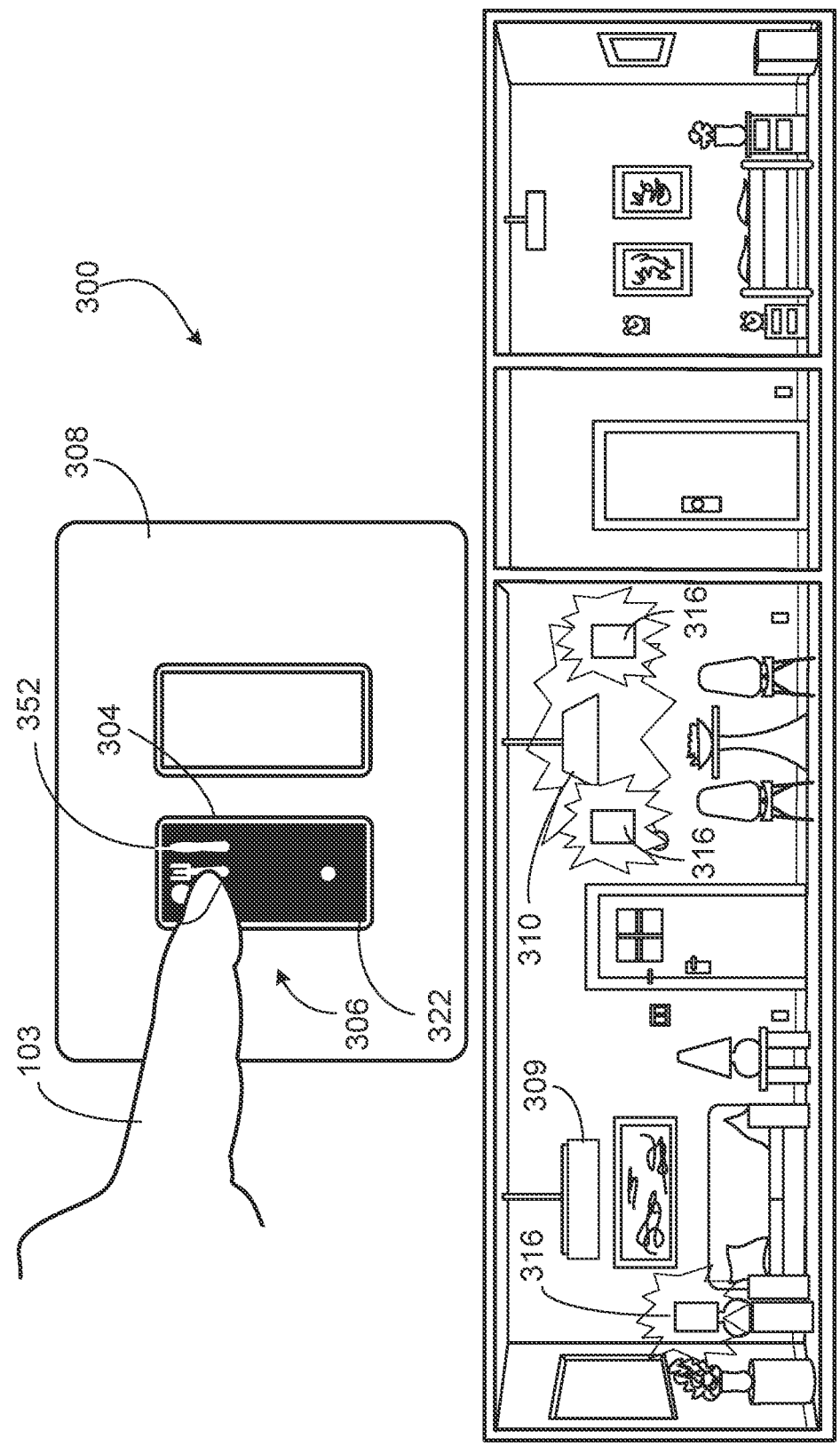

In FIG. 3A, the lighting control device 300 is connected to a base module positioned behind the wall plate 308. The lighting control device 300 includes a dynamic light switch actuator 306, operable in a manner similar to the light switch actuator discussed in connection with FIGS. 1A-2C, and an auxiliary light switch actuator. As demonstrated in FIG. 3A by the unilluminated outer actuation surface 322 of the light switch actuator 306 is inactive and not energized. In response to a user 103 moving the actuation surface 322 of the light switch actuator 306, the light switch actuator 306 begins to become energized, as shown in FIG. 3B. The energization or activation of the light switch actuator 306 is signaled by the power light indicator 305 and by full lighting setting icon 351. As shown in FIG. 3C where the icon 351 is fully lit (rather than partially lit as in FIG. 3B), the light switch actuator 306 is fully energized. In this particular configuration, the primary lights 309 and 310 are illuminated at full power. FIG. 3D shows the transition between lighting settings. As demonstrated in FIG. 3D, this transition is facilitated via user 103 completing swiping gesture 312 across the tactile display 304 and along the actuation surface 322. As the user completes the gesture 312, the icon 351 is swiped from the tactile display 304 as the tactile display toggles to a new light setting shown in FIG. 3E. The new light setting shown in FIG. 3E is represented or identified by the dinner icon 352. The new light setting shown in FIG. 3 has the light fixture 309 powered down and has caused lamp 316 and sconces 318 to become illuminated to change the lighting scene in the room. The change in the light setting causes a change in distribution of power to certain lighting fixture based on the selected lighting setting. The light switch actuator 306 may be pre-programmed with a plurality of lighting settings or may be configured with particular lighting settings as specified by the user 103. A further swiping gesture 315 shown in FIG. 3F or a different gesture are used to transition from the lighting setting of FIG. 3F represented by icon 352 to a further lighting setting.

Figure 4:
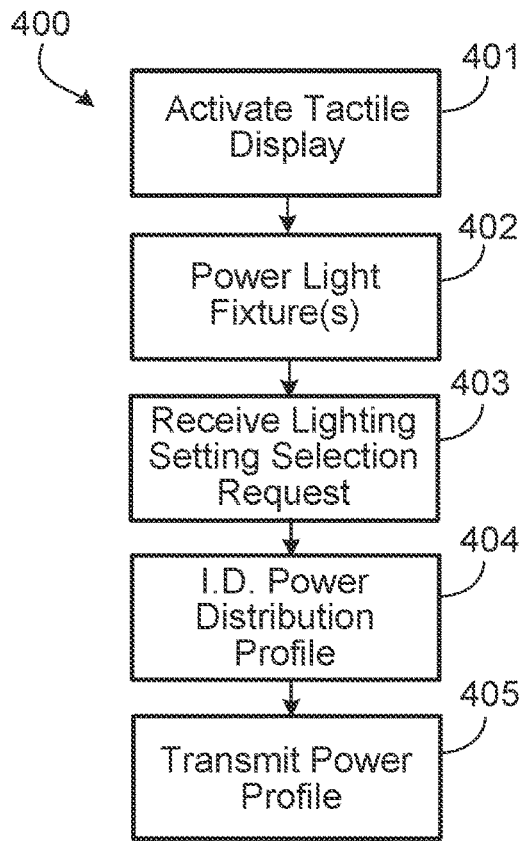
FIG. 4 provides a flow diagram of operations of a system for controlling a lighting control device.

FIG. 4 provides a flow diagram of operations of a system for controlling a lighting control device. FIG. 4 illustrates control operations of a control system, such as processor 130 configured to control the lighting control device 100 or 300, in accordance with various embodiments of the present invention. At 401, the tactile display housed in the light switch actuator is activated by moving the light switch actuator, for example by moving the actuation surface of the light switch actuator. At 402, the light fixtures electrically coupled to the light switch actuator via a base module are powered as the movement of the light switch actuator causes a contact component to move into a new position and thereby permit or cause an electrical flow path between a power source and the light fixture(s) to be closed. The tactile display housed in the light switch actuator is moved contemporaneously with the actuation surface. At 403, a lighting setting selection request is received via the tactile display, for example by a particular motion or motions on the tactile display. The lighting setting selection request identifies a lighting setting from among a plurality of lighting settings. A user may swipe multiple times to toggle through the plurality of lighting settings or may conduct a specific motion that corresponds to a particular lighting setting including, but not limited to, a half swipe and tap to achieve a light intensity of all the connected light fixtures at half of their peak output. The lighting settings identify distinct power distribution schemes for one or more light fixtures connected to the light switch module. At 404, a power distribution scheme is identified. At 405, the identified power distribution scheme is transmitted, for example by the base module responding to control signals from the light switch actuator, to adjust one, some, or all of the lights based on the power distribution scheme corresponding to the lighting setting selected. The power distribution schemes or profiles may be stored in a memory device of the lighting control device. In certain embodiments, the power distribution schemes may be adjusted to account for other parameters such as ambient lighting from natural light or an unconnected source. In certain embodiments the power distribution schemes may be adjusted based on one or more other sensor parameters. In particular embodiments, the lighting setting may be adjusted by automation based on time of day, sensed parameters such as light, temperature, noise, or activation of other devices including, but not limited to, any electronic device described herein.

Figure 5:
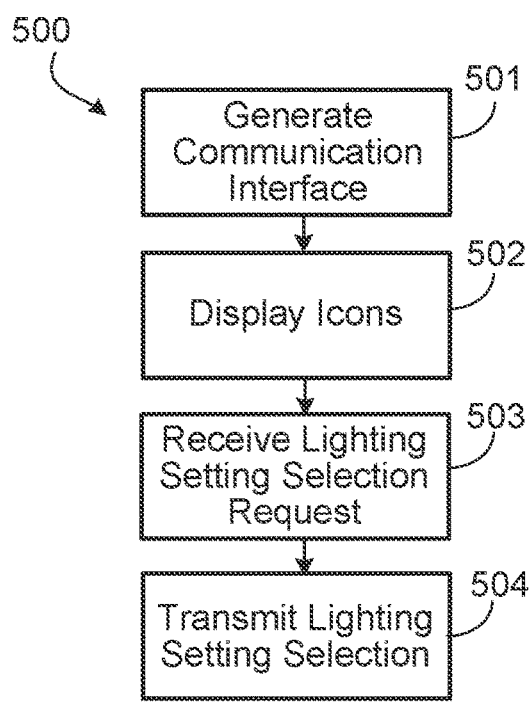
FIG. 5 shows a flow diagram of a system for remotely operating a lighting control device.

FIG. 5 shows a flow diagram of system for remotely operating a lighting control device. In particular embodiments, the lighting control device 100 or 300 may be operable from a remote device if the actuator switch is activated or energized. In such instances, the remote device may include one or more computer program applications, such as system 500, operating on the device to communicate with and control the lighting control device. Accordingly, at 501, the control system 500 initiates a connection module to generate a communication interface between a mobile electronic device and a light switch module. The connection module may cause the remote device to send one or more wireless transmission to the lighting control device via a communication protocol. At 502, the control system 500 causes the remote device to generate a display of icons on a display device of the mobile electronic device to facilitate selection of a lighting setting. At 503, the control system 500 receives a lighting setting selection based on the user selecting a particular icon. At 504, a transmission module causes the lighting setting selected to be transmitted to the lighting control device so that the light switch module and/or the base module can cause the power distribution scheme corresponding to the lighting setting to be transmitted to the lighting fixtures. The tactile display of the lighting control device may be updated in concert with receipt of the lighting setting to display the icon selected on the mobile electronic device and corresponding to the lighting setting selected on the tactile device.

Figure 6:
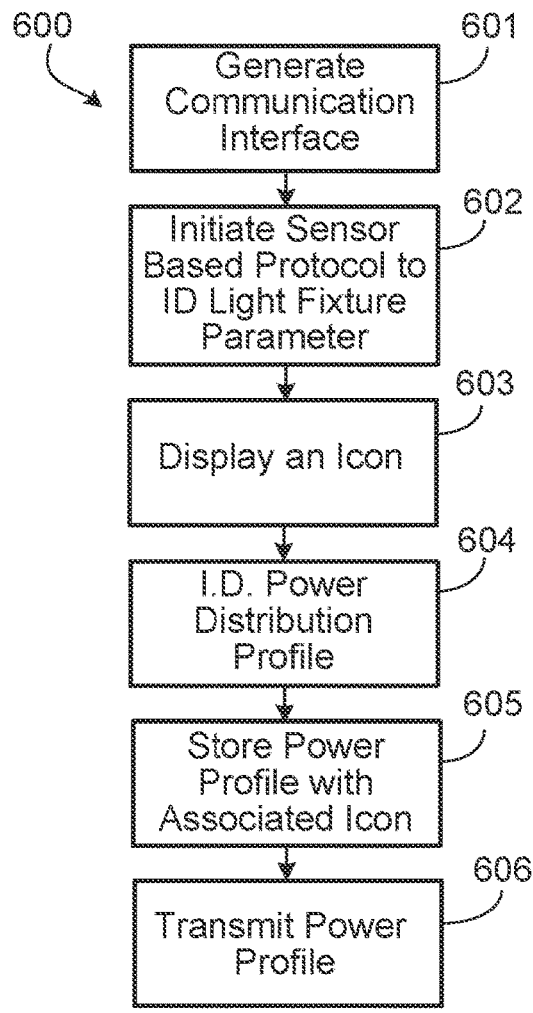
FIG. 6 illustrates a flow diagram of a system for remotely configuring operations of a lighting control device.

FIG. 6 illustrates a flow diagram of a system for remotely configuring operations of a lighting control device. The remote device may include devices including, but not limited to a mobile phone, a mobile computing device or a computing device remote from the light control device. At 601, the mobile electronic device generates a communication interface with the light switch module. At 602, a light fixture identification module initiates a sensor based protocol to identify a parameter associated with one or more light fixtures connected to the light switch control module. At 603, a display selection module causes a display of an icon to appear on a display device of the mobile electronic device. At 604, a lighting setting configuration module allows a user to create a power distribution scheme or profile for the light fixtures identified based on the identified parameters and a user specified input related to light intensity. At 604, a storage module is used to the store the power distribution scheme and associate a particular lighting setting icon with the power distribution scheme. At 605, a transmission module transmits the power distribution scheme and the associated icon to the light switch control module.

FIGS. 7A and 7B are schematics of light control systems. The lighting control system 702 is configured as a lamp plug and includes a base housing 712 having an electrical plug 706 extending there from for connecting the system 702 with an electrical wall outlet 720. The lighting control system 702 includes an electrical outlet 703 for receiving an electrical plug from a lamp 711 from a lamp 710. The base housing 712 is in the form of a puck or disk that is configured for being positioned on the floor. The lighting control system 702 is configured to wireless communicate with other lighting control systems. The lighting control system 702 is configured to sense various signals 707 (e.g. sound, light, etc.) including, but not limited to, vibrations 705 transmitted through a floor surface. FIG. 7B is a modified version of the lighting control system 702 that is configured to receive a lighting control device 704, for example that corresponds to switch module 102, in which case lighting control device 702 can operate in manners similar to switch base module 112.

Figure 8:
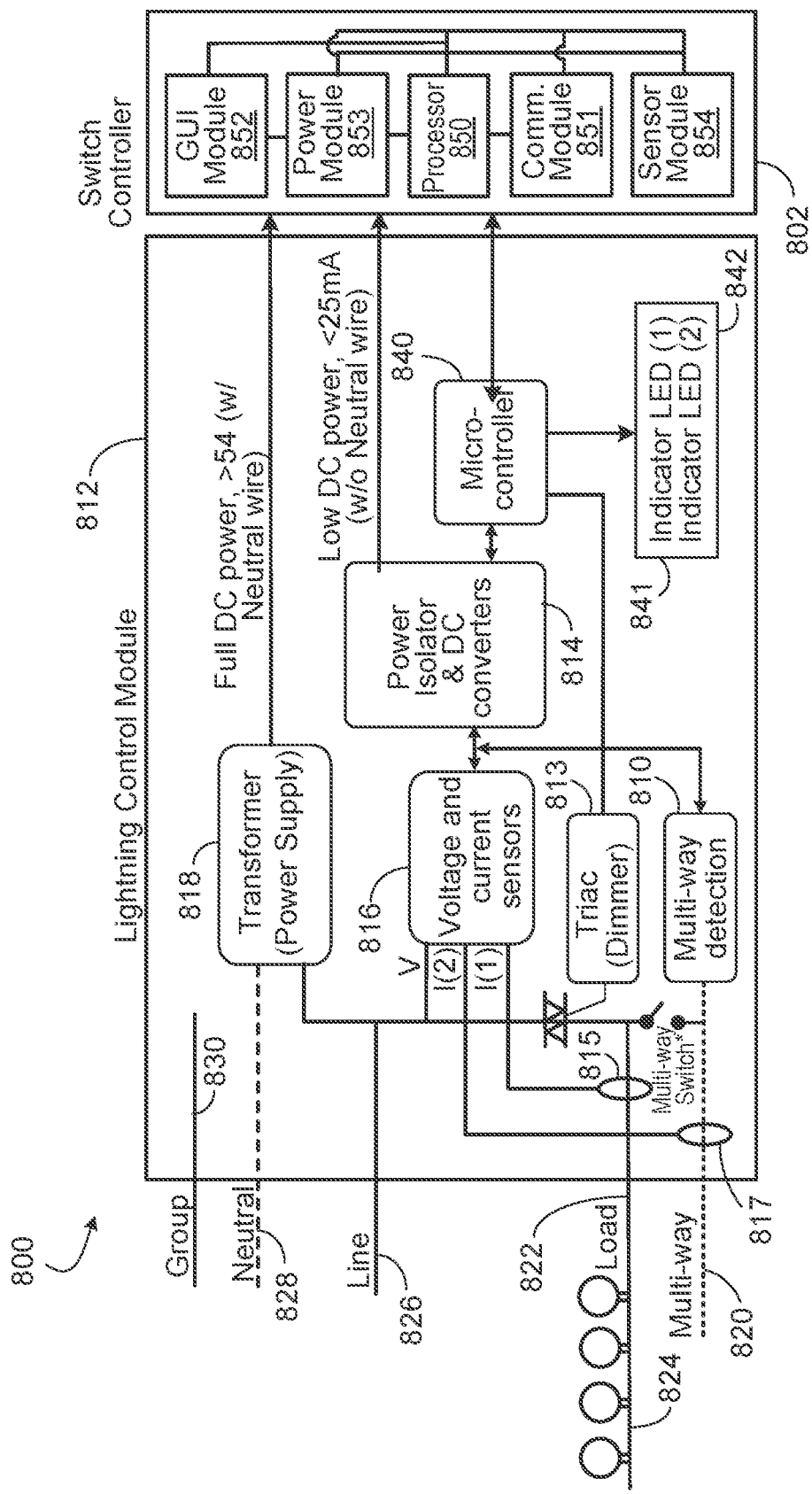
FIG. 8 is a schematic of a lighting control system.

FIG. 8 is a schematic of a lighting control system 800 configured to execute certain lighting control operations described herein. The lighting control system 800 illustrates lighting control system components that can be implemented with a lighting control system including an air gap system as described herein. The lighting control system 800 is depicted separated into a base lighting control module 812 (which may be configured in a manner similar to base module 112) and a switch module or switch controller 802 (which may be configured in a manner similar to switch module 102). As described herein, the switch module 802 can include a tactile interface, operable via the graphical user interface module 852, and a switch actuator, such as the tactile display 104 and the light switch actuator 106 described herein. The switch module 802 houses a processor 850, which may be configured to send commands to microcontroller 840 and receive inputs from the microcontroller 840 to control the operation of a transformer 818, a power isolator and an AC to DC converter 814 (which may include a flyback converter), and a dimmer, such as a TRIAC dimmer 813, a voltage and current sensor 816. In some embodiments, the base lighting control module 812 may include a MOSFET dimmer. The power isolator 814 separates the analog AC current from the low power or DC digital components in the base lighting control module 812 and the switch module 802. The power isolate 814 may provide power inputs to the switch control module 802 via a power module 853. Power module 853 includes power circuitry configured to regulate the flow of power from the base module 812 to the switch controller module 802 including directing power to one or more of the modules in the switch controller module 802. The switch module 802 also houses a communication module, which can include one or more antennae or other wireless communication modules. The switch module 802 also houses a sensor module, which can include one or more sensors, such as a light sensor, a camera, a microphone, a thermometer, a humidity sensor, and an air quality sensor. The processor 850, is communicably coupled with one or more modules in the switch module 802 to control the operation of and receive inputs from those modules, for example to control modulation of the flow of electrical energy to a lighting circuit of a light fixture 824 connected to the base lighting control module 812.

The base lighting control module 812 includes a ground terminal 830 for grounding various electrical components container in the module 812. The base light control module 812 includes a neutral terminal 828 for connecting to a neutral wire, a line terminal 826, and a load terminal 822. As shown in FIG. 8, the voltage and current sensor(s) are coupled to the load line to detect changes in the voltage or current along the line carrying power to one or more light fixtures 824 connected to the lighting circuit (750). The base lighting control module 812 also includes a controller 840 communicably coupled to the processor 850. The base lighting control module 812 also includes LED indicator lights 842 and 841 for indicating information regarding the status of the base lighting control module 812. For example, in some embodiments LED indicator light 841 can indicates if a neutral wire is connected while LED indicator light 842 can indicate if a 3 way connection is connected.

Figure 9A:
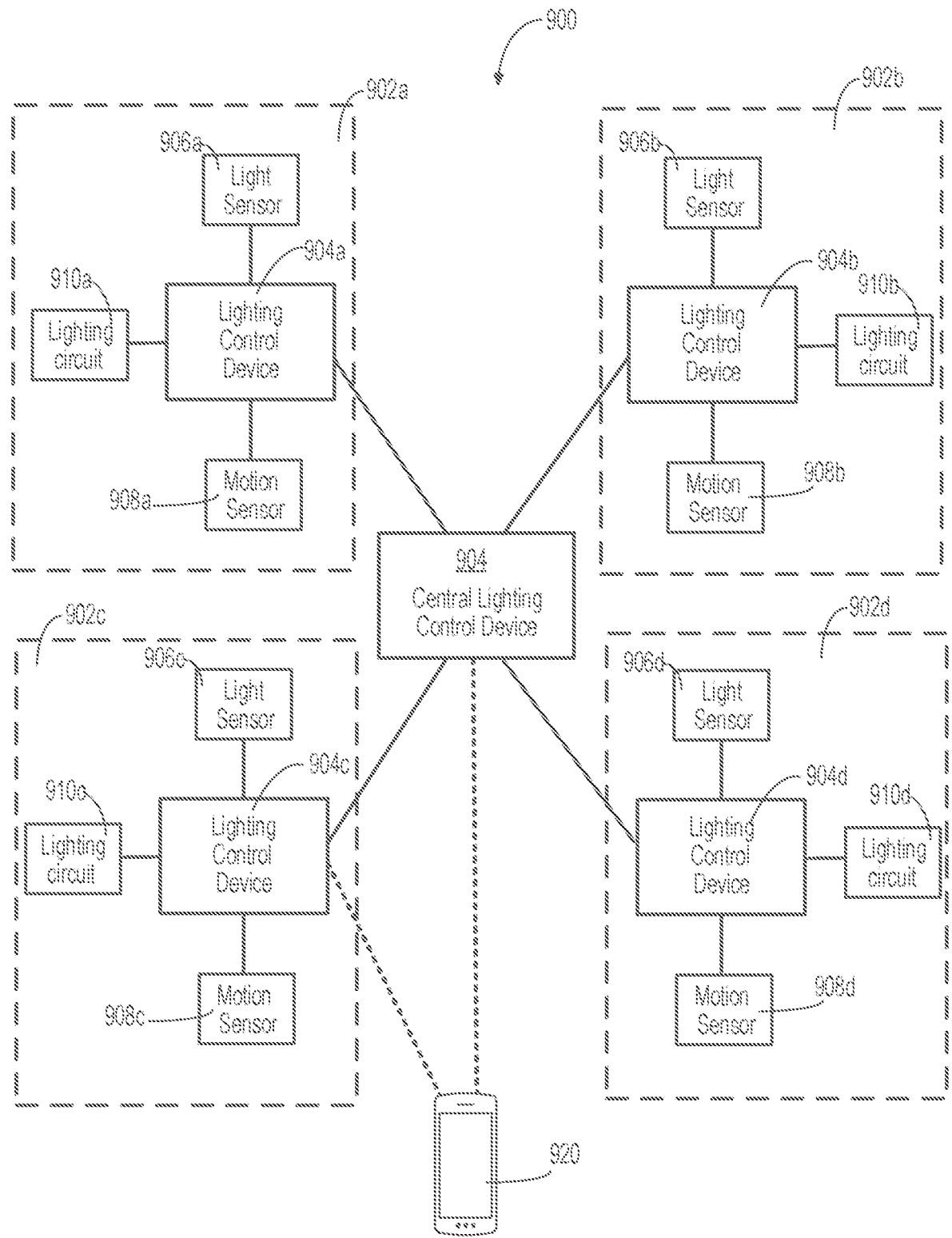
FIGS. 9A and 9B illustrate lighting control systems that include multiple lighting control devices.

FIG. 9 describes an implementation of lighting control system 900 that includes multiple lighting control subsystems that are distributed over a building (e.g., house, office etc.), for example, in different rooms of the building. In the implementation of the lighting control system 900 illustrated in FIG. 9A, rooms 902*a*-*d* have distinct lighting control systems. For example, the lighting control system of room 902*a* includes lighting control device 904*a*, lighting circuit 910*a*, light sensors 906*a* and motion sensors 908*a*. The lighting control system 900 can include a central lighting control device 904 that serves as a central control for the lighting control system 900. In certain embodiments, the central lighting control device 904 can include a lighting control system such as system 100 or 800.

The lighting control system of room 902*a*, which comprises lighting control device 904*a*, light sensor 906*a*, motion sensor 908*a* and lighting circuit 910*a*, is discussed. However, the concepts and applications discussed are not limited to the lighting control system in the room 902*a* and can be generally applied to lighting control systems in other rooms (e.g., 902b-d) or lighting control subsystems that may distributed over more than one room.

The light sensor 906a is configured to detect ambient light (which can include natural light and/or light from a light fixture connected to the lighting circuit 910a), for example by converting the electromagnetic energy (e.g., photon energy) into an electrical signal (e.g., a current or a voltage signal). The electrical signal can be communicated to the lighting control device 904a. The light sensor 906a can include one or more photo-resistors, photodiodes, charge coupled devices etc. The light sensor 906a can include a light filter that preferentially allows certain frequencies of light to be transmitted and therefore detected by the light sensor 906a. For example, the light filter can be configured to transmit frequencies that correspond to the light emanating from the lighting circuit 910a. This can allow the light sensor (e.g. 906a) to preferentially detect light from the lighting circuit 910a while filtering out light generated by other sources. For example, if the light sensor is located in a room that receives ambient natural light (e.g., daylight), the light sensor can substantially filter out the ambient natural light and primarily detect light from the lighting circuit 910a. The light sensor 906a can also be configured to efficiently and accurately detect a range of light intensities, for example, the range of intensities that can be produced by the lighting circuit 910a. This can allow the light sensor 906a to efficiently and accurately detect light for various intensity settings of the lighting circuit 910a.

The motion sensor 908a can be configured to detect motion in the room 902a. For example, the motion sensor can detect movement of an occupant in the room 902a. The motion sensor 908a can include one or more of passive sensors (e.g., passive infrared (PIR) sensor), active sensors (e.g., microwave (MW) sensor, ultrasonic sensors etc.) and hybrid sensors that include both passive and active sensor (e.g., Dual Technology Motion sensors). The passive sensors do not emit any energy and detect changes in energy of the surrounding. For example, a PIR sensor can detect infrared energy emitted by the human body (due to the temperature associated with the human body). Active sensors, on the other hand, emit electromagnetic or sonic pulses and detect the reflection thereof. For example, MW sensor emits a microwave pulse and detects its reflection. Hybrid sensors can include both active and passive sensors and therefore motion can be sensed both actively and passively (hybrid sensing). Hybrid sensing can have several advantages, for example, the probability of false positive detection of motion can be smaller in hybrid sensors compared to active/passive sensors.

The lighting control device 904a is configured to communicate with the light sensor 906a and motion sensor 908a. The motion sensor 908a can send a notification signal to the lighting control device 904a conveying that motion has been detected in an area proximal to the lighting circuit 910a, for example, in the room 902a. The light sensor 906a can send a notification signal to the lighting control device 904a conveying that light emanating from the lighting circuit 910a has been detected. Additionally, the notification signal can include information about the properties of the detected light, e.g., intensity, bandwidth etc. The lighting control device 904a can store data representative of the notification signals received from the motion and light sensors in a device database. The lighting control device 904a can include a clock and/or a timer that allows the lighting control device 904a to track the time and/or duration of the received signals from the light sensor 906a and motion sensor 908a. The tracking time and/or duration information can be also be stored in the device database.

The lighting control device 904a can be configured to receive and transmit data through the internet. The lighting control device 904a can, for example, infer information about ambient natural light from data about the weather conditions, daylight hours etc. from online databases (e.g., databases of weather.gov, gaisma.com, noaa.gov wunderground.com etc.). For example, the received data can include information about the sunrise and sunset times in the geographical area associated with the lighting control system 900 and the time of the year. Based on this, the lighting control circuit 904a can infer the time period during which no ambient natural light is available. In another example, the received data can contain information about the weather conditions. The lighting control circuit 904a can infer, for example, that overcast conditions can lead to reduction in natural ambient light. The lighting control device 904a can save the data and/or inferred information in the device database. This can allow the lighting control device 904a to infer patterns between the usage of the lighting circuit 910a and ambient natural light conditions.

The lighting control device 904a can be configured to determine one or more properties of the lighting circuit 910a. For example, device 904a can determine the type (e.g., incandescent, fluorescent, LED, halogen, high intensity discharge, full spectrum, UV, black light, antique, vintage) and the wattage of the light bulbs associated with the lighting circuit 910a. The light control device 904a can also search online databases for information about the detected light bulbs. For example, the lighting control device 904a can download specifications (e.g., information about voltage, wattage, luminescence, dimmability, average life etc.) from online databases of the manufacturers of the detected light bulb. The lighting control device 904a can also download information related to the light and motion sensors, for example, drivers associated with the light and motion sensors. The determined properties and the downloaded information about the lighting circuit 910a can be stored in the device database.

The lighting control device 904a can be configured to receive data and/or instructions from communication device 920 (e.g., cellphone, laptop, iPad, input device such as keypad, touch screen etc.). Additionally or alternately, communication device 920 can be input device (e.g., keypad, touchscreen etc.). For example, the computation device 920 may provide instructions for the operation of the lighting control device 904a. Based on the instruction, the lighting control device 904a can switch on/off one or more light bulbs in the lighting circuit 904a. The computation device 920 can also instruct the lighting control device 904a to change the operation parameters of the lighting circuit 910a. For example, the lighting control device 904a can be instructed to increase/decrease the brightness of the lighting circuit 904a (e.g., by increasing/decreasing the power suppled to the lighting circuit). The communication device 920 can instruct the lighting control device 904a to perform one or more of the aforementioned functions at a certain time or after a certain period of time. For example, the communication device 920 can instruct the lighting control device 904a to set up a timer at the end of which a desired function is performed. Through the communication device 920, information related to the lighting control system 900 can be conveyed to the lighting control device 904a. For example, a user can input the room-types (e.g., bedroom, kitchen, living room etc.) of the rooms 902a-d. The user shutdown one or more the lighting control subsystems in room 902a-d for a desired period of time, for example, when the user will be away for a vacation. The communication device 920 can communicate with the lighting control device 904a using short-range wireless technology (Bluetooth, Wi-Fi etc.), through a cellular network and/or a physical connection (e.g., Ethernet cable). The data and/or instruction received by the lighting control circuit 904a from the communication device 920 can be stored in the device database. The time at which the data and/or instruction were received can also be stored in the device database.

The lighting control device 904a can be configured to communicate information to the communication device 920 and/or an output screen. For example, the lighting control device 904a may communicate the operational parameters associated with the lighting circuit 910a (e.g., brightness of the lighting circuit 910a, tentative time at which the lighting circuit 910a will be turned on/off, duration of operation of the lighting circuit 910a etc.). The lighting control device 904a can communicate notification signal from the light sensor 906a and motion sensor 908a to the communication device 920. For example, communication device 920 can be notified that motion or light has been detected in room 902a.

The central lighting control device 904 can communicate with the lighting control subsystems distributed over the building (e.g., rooms 902a-d), and provide a central control for the lighting control system 900. The central lighting control device 904 can control the operation of light sensors 906a-d, motion sensors 908a-d, lighting circuits 910a-d and lighting control devices 904a-d. For example, the central lighting control device 904 can instruct the lighting control device 904a to change the operating parameters of the lighting circuit 910a. The central lighting control device 904 can also receive notification signals from light sensors 906a-d and motion sensors 908a-d, and communication device 920.

Figure 9B:
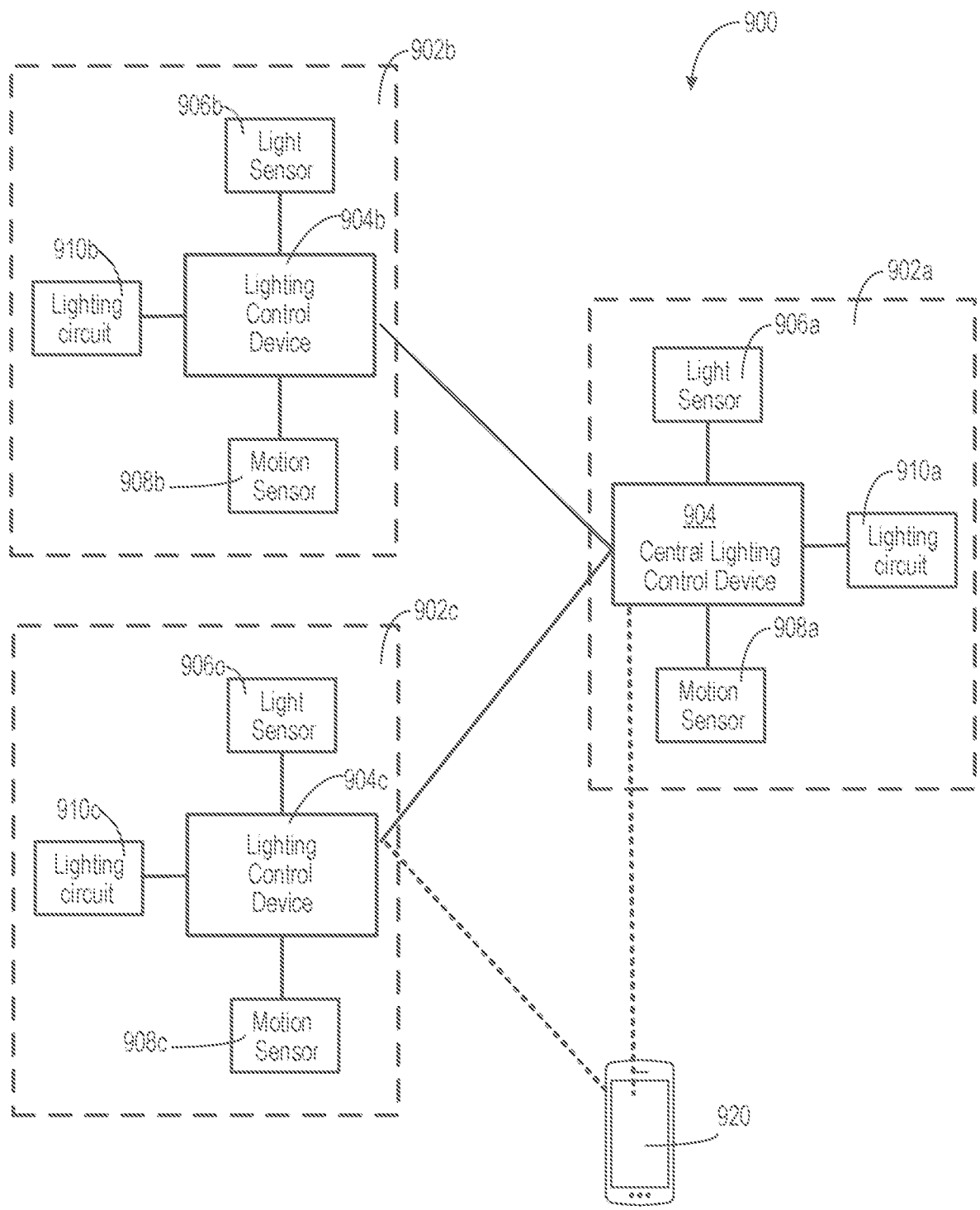

The central lighting control device 904 can include a central device database. Data stored in device databases associated with lighting control devices 904a-d can be transferred, for example, periodically, to the central device database. In some implementation, the central lighting control device can request specific information from the device databases of lighting control devices. For example, the central control device 904 can request the lighting control device 904a for information related to one or more of light sensors 906a, motion sensors 908a, instructions from communication device 920, etc. FIG. 9B illustrates another implementation of the lighting control system 900. In this implementation the central light control device 904 also operates as the "lighting control device" for the lighting control subsystem associated with room 902a (which includes light sensor 906a, motion sensor 908a and lighting circuit 910a).

Figure 10:
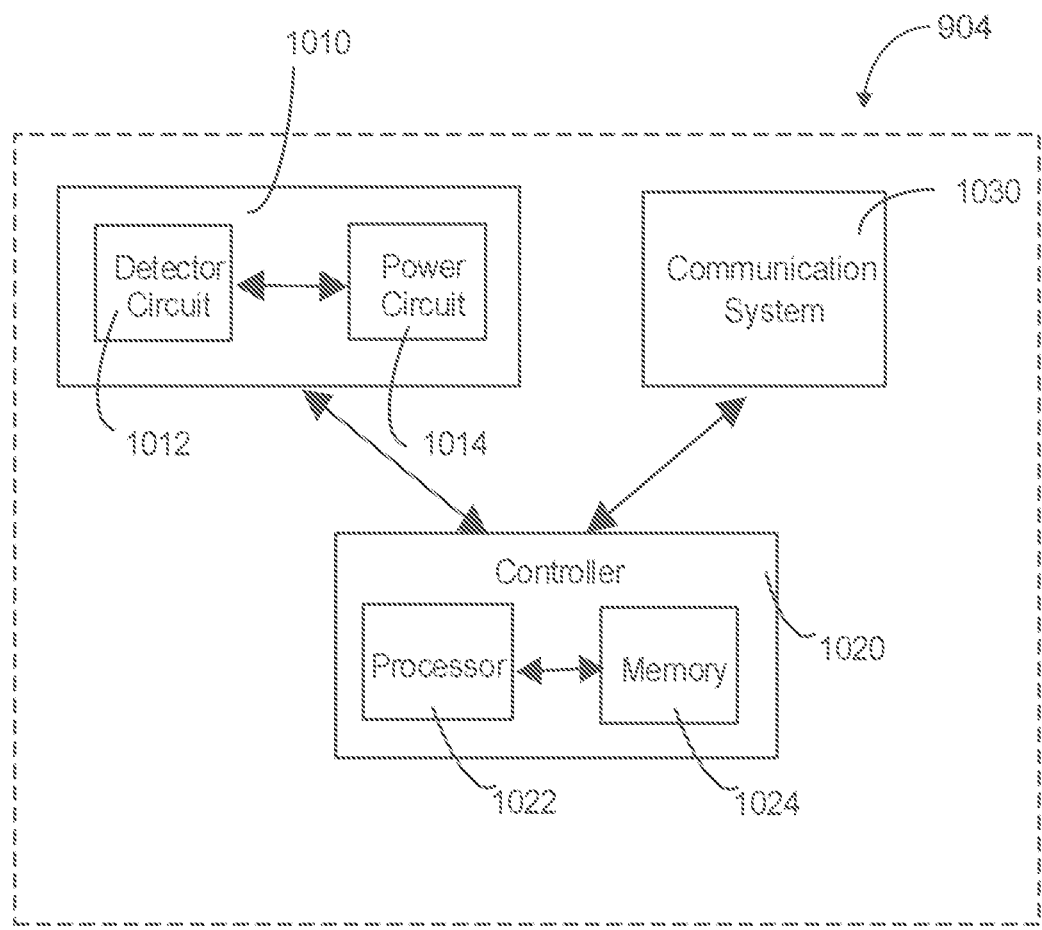
FIG. 10 schematically illustrates a lighting control device.

FIG. 10 illustrates an implementation of the central lighting control device 904 as described in FIG. 9B. The central lighting control device 904 comprises lighting circuit system 1010, controller 1020 and communication system 1030. The controller 1020 can control the operation of and receive data from the lighting circuit system 1010 and communication system 1030. The controller 1020 includes a processor 1022 and a storage device 1024. The processor is configured to run applications that control the operation of the lighting control system 900, and the storage device 1024 can store data related to the lighting control system 900 (e.g., central device database, device database etc.).

The lighting circuit system 1010 can transmit electrical power to and detect response of the lighting circuit 910a. The lighting circuit system 1010 can include a power circuit 1014 that can supply power to the lighting circuit 910a, and a detector circuit 1012 that can detect the response of the lighting circuit 910a. The power circuit 1014 can comprise a tunable voltage/current source that can supply an input voltage/current signal to the lighting circuit 910a. The detector circuit 1012 is configured to detect a response of the lighting circuit 910a that can include one or more of current, voltage and impedance response. In some implementations, the detector circuit 1012 may include a voltage sensing circuit that can detect a voltage response (e.g., voltage across the lighting circuit 910a) or a current sensing circuit that can detect a current response (e.g., the current flowing into the lighting circuit 910a). The power circuit 1014 can also supply power to the light sensor 906a and the voltage sensor 908a.

The communication system 1030 is configured to communicate with light sensor 906a, motion sensor 908a, and lighting control devices (e.g., 910a-d in FIG. 9A, 910b-d in FIG. 9B). For example, the communication system 1030 (e.g., antenna, router etc.) can transmit instructions (e.g., instruction to detect light/motion) from the controller 1020 to the light sensor 906a and/or motion sensor 908a. The instructions can be transmitted wirelessly in the 2.4 GHz ISM band using various wireless radio technologies (Wi-Fi, Bluetooth, Low Power Radio (LPR) etc.). Additionally or alternately, the instructions can be transmitted in the form of an electrical signal (e.g., current signal, voltage signal) or optical signal through a physical connection (e.g., transmission line, Ethernet cable etc.). The communication system 930 can be configured to receive notification signals (e.g., through the channels of instruction transmission described above) from the light sensors 906a and/or motion sensors 908a and convey the notification signal to the controller 1020.

The communication system 1030 can also be configured to communicate with communication device 920, for example, through a cellular network, wireless radio technology etc. The communication system 1030 can include, for example, a router that allows it to communicate through the internet with websites and online databases. For example, the controller 1020 can instruct the communication system 1030 to access the website of a light bulb manufacturing (e.g., light bulb in the lighting circuit 910a) and download the relevant specifications. The communication system 1030 can also, for example, download software (e.g., drivers) that can allow the controller 1020 to communicate with the light sensors 906a and motion sensors 908a. The communication system 1030 can also download updated operating systems for the controller 1020.

The lighting control device 904 can control the operation of lighting circuits 910a-d based on notification signals from the light sensors 906a-d and motion sensors 908a-d. For example, if the lighting circuit 910a has been switched on and no motion is observed by the motion sensor 908a for a predetermined period of time, the control device 904 can automatically switch off the lighting circuit 910a. The control device 904 can make the determination that the lighting circuit 910a has been switched on based on notification signal from the light sensor 906a and/or the response from the detector circuit 1012. The period of time between the last detected motion and the time at which the lighting circuit 910a is switched off can be based on, for example, an input provided by a user through the communication device 920. This period of time can be different for different rooms. For example, the period of time can be longer for the room 902a (e.g., bedroom) compared to the room 902b (e.g., a bathroom).

The lighting control system 900 can be configured to control the operation of the lighting circuits 910a-d based on analysis of the behavior of one or more users of the system 900 and data acquired by the system 900. The behavior analysis can include, for example, pattern recognition of the notification signals from the light sensors 906a-d and motion sensors 908a-d, instructions provided by the user through communication device 920 and information obtained by lighting control device 904 from online databases. For example, the central lighting control device 904 can be notified by the light sensor 906a that the lighting device 910a is switched off at approximately a certain time during the weekdays and at approximately a different time during the weekends. Based on this pattern, the lighting control device 904 can set switch off times, which are different for weekends and weekdays, for automatically switch off the light 910a. Automatic switching off the light 910s can be suspended if motion is detected by motion sensor 908a, and notification can be sent to the communication device 920.

The control device 904 can also include information obtained from online databases in its behavioral analysis of the users. For example, the control device 904 can be notified that the user switches on the light 910a in the mornings of certain days in the year. The device 904 compares this behavior with the weather conditions (known through online databases) and determines that the light 910a is switched on in the mornings of days when the sky is overcast. Based on this pattern, the control device 904 can automatically switch on the light 910a on days when the sky is over cast. Additionally, the control device 904 may learn that the weather conditions effect the operation of lighting circuit 910a but not of lighting circuit 910b. This may arise from the fact the room 902a, associated with lighting circuit 910a, has windows and receives natural ambient light, while room 902b, associated with lighting circuit 910b, does not have windows and does not receive natural ambient light. The control device 904 can infer that the operation of lighting circuit 910b is independent of weather conditions. In some implementations, the control device 904 can change the operating parameters of lighting circuit 910a based on weather conditions. For example, the control device 904 can change the brightness setting of the lighting circuit 910b based on the weather conditions.

Figure 11:
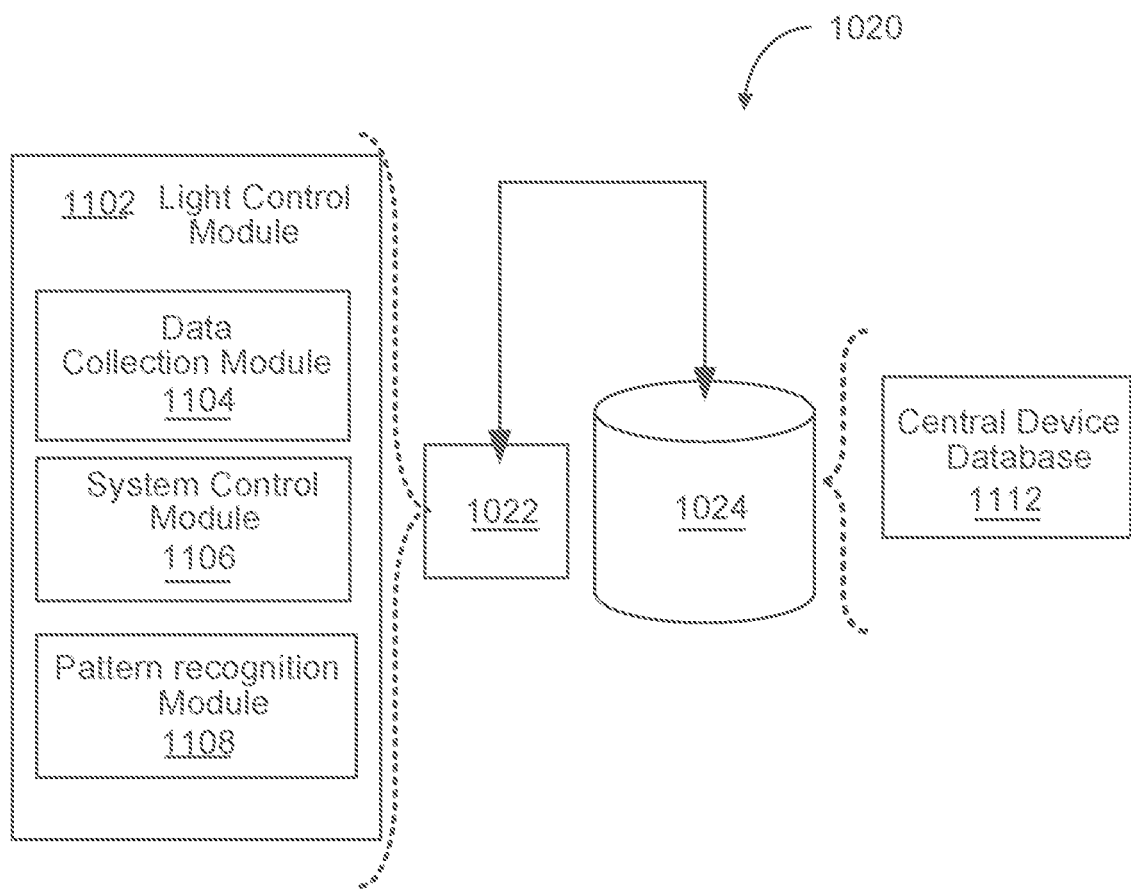
FIG. 11 schematically illustrates a block diagram of the processes run by a controller of the lighting control device.

FIG. 11 illustrates the controller 1020 comprising the processor 1022 and the storage device 1024 and configured to execute light control module 1102. The light control module 1102 can collect, store and analyze data, and determine the operation of a lighting circuit (e.g., lighting circuit 910a). The light control module 1102 can include a data collection module 1104, system control module 1106, and pattern recognition module 1108. The data collection module can collect data (e.g., data from online databases, detector circuit 1012, communication device 920, notification signals from light sensors 906a-d and motion sensors 908a-d etc.) from the communication system 1030 and store the data in the central device database 1112 in storage device 1024. The system control module 1106 controls the operation of lighting circuit system 1010. For example, system control module 1106 can instruct the power circuit 1014 to change the electrical power supplied to the lighting circuit 910a. The system control module 906 can determine, based on voltage/current response of the lighting circuit 910a measured by the detector circuit 1012, the type of light bulbs (e.g., incandescent, fluorescent, LED, halogen, high intensity discharge, full spectrum, UV, black light, antique, vintage) therein and store this information in the central device database 1112. The system control module 1106 can also control the operation of the light sensors 906a-d and motion sensors 908a-d. For example, it can instruct the light and motion sensors to start or suspend detection of light and motion signals. The pattern recognition module 1108 can include machine learning techniques that use data in the central device database 1112 as "training data" to infer patterns based on which the operating parameters for the lighting circuits 910a-d can be determined.

Implementations of the subject matter and the operations described in this specification can be implemented by digital electronic circuitry, or via computer software, firmware, or hardware, including the structures disclosed in this specification and their structural equivalents, or in combinations of one or more of them. Implementations of the subject matter described in this specification can be implemented as one or more computer programs, i.e., one or more modules of computer program instructions, encoded on computer storage medium for execution by, or to control the operation of, data processing apparatus.

A computer storage medium can be, or be included in, a computer-readable storage device, a computer-readable storage substrate, a random or serial access memory array or device, or a combination of one or more of them. Moreover, while a computer storage medium is not a propagated signal, a computer storage medium can be a source or destination of computer program instructions encoded in an artificially generated propagated signal. The computer storage medium can also be, or be included in, one or more separate physical components or media (e.g., multiple CDs, disks, or other storage devices).

The operations described in this specification can be implemented as operations performed by a data processing apparatus on data stored on one or more computer-readable storage devices or received from other sources.

The term "data processing apparatus" encompasses all kinds of apparatus, devices, and machines for processing data, including by way of example a programmable processor, a computer, a system on a chip, or multiple ones, or combinations, of the foregoing. The apparatus can include special purpose logic circuitry, e.g., an FPGA (field programmable gate array) or an ASIC (application specific integrated circuit). The apparatus can also include, in addition to hardware, code that creates an execution environment for the computer program in question, e.g., code that constitutes processor firmware, a protocol stack, a database management system, an operating system, a cross-platform runtime environment, a virtual machine, or a combination of one or more of them. The apparatus and execution environment can realize various different computing model infrastructures, such as web services, distributed computing and grid computing infrastructures.

A computer program (also known as a program, software, software application, script, or code) can be written in any form of programming language, including compiled or interpreted languages, declarative or procedural languages, and it can be deployed in any form, including as a stand-alone program or as a module, component, subroutine, object, or other unit suitable for use in a computing environment. A computer program may, but need not, correspond to a file in a file system. A program can be stored in a portion of a file that holds other programs or data (e.g., one or more scripts stored in a markup language document), in a single file dedicated to the program in question, or in multiple coordinated files (e.g., files that store one or more modules, sub programs, or portions of code). A computer program can be deployed to be executed on one computer or on multiple computers that are located at one site or distributed across multiple sites and interconnected by a communication network.

The processes and logic flows described in this specification can be performed by one or more programmable processors executing one or more computer programs to perform actions by operating on input data and generating output. The processes and logic flows can also be performed by, and apparatus can also be implemented as, special purpose logic circuitry, e.g., a FPGA (field programmable gate array) or an ASIC (application specific integrated circuit).

Processors suitable for the execution of a computer program include, by way of example, both general and special purpose microprocessors, and any one or more processors of any kind of digital computer. Generally, a processor will receive instructions and data from a read only memory or a random access memory or both. The essential elements of a computer are a processor for performing actions in accordance with instructions and one or more memory devices for storing instructions and data. Generally, a computer will also include, or be operatively coupled to receive data from or transfer data to, or both, one or more mass storage devices for storing data, e.g., magnetic, magneto optical disks, or optical disks. However, a computer need not have such devices. Moreover, a computer can be embedded in another device, e.g., a mobile telephone, a personal digital assistant (PDA), a mobile audio or video player, a game console, a Global Positioning System (GPS) receiver, or a portable storage device (e.g., a universal serial bus (USB) flash drive), to name just a few. Devices suitable for storing computer program instructions and data include all forms of non-volatile memory, media and memory devices, including by way of example semiconductor memory devices, e.g., EPROM, EEPROM, and flash memory devices; magnetic disks, e.g., internal hard disks or removable disks; magneto optical disks; and CD ROM and DVD-ROM disks. The processor and the memory can be supplemented by, or incorporated in, special purpose logic circuitry.

To provide for interaction with a user, implementations of the subject matter described in this specification can be implemented on a computer having a display device, e.g., a CRT (cathode ray tube) or LCD (liquid crystal display) monitor, for displaying information to the user and a keyboard and a pointing device, e.g., a mouse or a trackball, by which the user can provide input to the computer. Other kinds of devices can be used to provide for interaction with a user as well; for example, feedback provided to the user can be any form of sensory feedback, e.g., visual feedback, auditory feedback, or tactile feedback; and input from the user can be received in any form, including acoustic, speech, or tactile input. In addition, a computer can interact with a user by sending documents to and receiving documents from a device that is used by the user; for example, by sending web pages to a web browser on a user's user device in response to requests received from the web browser.

Implementations of the subject matter described in this specification can be implemented in a computing system that includes a back end component, e.g., as a data server, or that includes a middleware component, e.g., an application server, or that includes a front end component, e.g., a user computer having a graphical display or a Web browser through which a user can interact with an implementation of the subject matter described in this specification, or any combination of one or more such back end, middleware, or front end components. The components of the system can be interconnected by any form or medium of digital data communication, e.g., a communication network. Examples of communication networks include a local area network ("LAN") and a wide area network ("WAN"), an internetwork (e.g., the Internet), and peer-to-peer networks (e.g., ad hoc peer-to-peer networks).

The computing system can include users and servers. A user and server are generally remote from each other and typically interact through a communication network. The relationship of user and server arises by virtue of computer programs running on the respective computers and having a user-server relationship to each other. In some implementations, a server transmits data (e.g., an HTML page) to a user device (e.g., for purposes of displaying data to and receiving user input from a user interacting with the user device). Data generated at the user device (e.g., a result of the user interaction) can be received from the user device at the server.

While this specification contains many specific implementation details, these should not be construed as limitations on the scope of any inventions or of what may be claimed, but rather as descriptions of features specific to particular implementations of particular inventions. Certain features that are described in this specification in the context of separate implementations can also be implemented in combination in a single implementation. Conversely, various features that are described in the context of a single implementation can also be implemented in multiple implementations separately or in any suitable sub combination. Moreover, although features may be described above as acting in certain combinations and even initially claimed as such, one or more features from a claimed combination can in some cases be excised from the combination, and the claimed combination may be directed to a sub combination or variation of a sub combination.

For the purpose of this disclosure, the term "coupled" means the joining of two members directly or indirectly to one another. Such joining may be stationary or moveable in nature. Such joining may be achieved with the two members or the two members and any additional intermediate members being integrally formed as a single unitary body with one another or with the two members or the two members and any additional intermediate members being attached to one another. Such joining may be permanent in nature or may be removable or releasable in nature.

It should be noted that the orientation of various elements may differ according to other exemplary implementations, and that such variations are intended to be encompassed by the present disclosure. It is recognized that features of the disclosed implementations can be incorporated into other disclosed implementations.

While various inventive implementations have been described and illustrated herein, those of ordinary skill in the art will readily envision a variety of other means and/or structures for performing the function and/or obtaining the results and/or one or more of the advantages described herein, and each of such variations and/or modifications is deemed to be within the scope of the inventive implementations described herein. More generally, those skilled in the art will readily appreciate that all parameters, dimensions, materials, and configurations described herein are meant to be exemplary and that the actual parameters, dimensions, materials, and/or configurations will depend upon the specific application or applications for which the inventive teachings is/are used. Those skilled in the art will recognize, or be able to ascertain using no more than routine experimentation, many equivalents to the specific inventive implementations described herein. It is, therefore, to be understood that the foregoing implementations are presented by way of example only and that, within the scope of the appended claims and equivalents thereto, inventive implementations may be practiced otherwise than as specifically described and claimed. Inventive implementations of the present disclosure are directed to each individual feature, system, article, material, kit, and/or method described herein. In addition, any combination of two or more such features, systems, articles, materials, kits, and/or methods, if such features, systems, articles, materials, kits, and/or methods are not mutually inconsistent, is included within the inventive scope of the present disclosure.

Also, the technology described herein may be embodied as a method, of which at least one example has been provided. The acts performed as part of the method may be ordered in any suitable way. Accordingly, implementations may be constructed in which acts are performed in an order different than illustrated, which may include performing some acts simultaneously, even though shown as sequential acts in illustrative implementations.

The claims should not be read as limited to the described order or elements unless stated to that effect. It should be understood that various changes in form and detail may be made by one of ordinary skill in the art without departing from the spirit and scope of the appended claims. All implementations that come within the spirit and scope of the following claims and equivalents thereto are claimed.

What is claimed is:

1. A lighting control system comprising:
   a base housing configured for positioning on a floor surface;
   a base electrical plug extending from the base housing and configured for plugging into a wall electrical outlet;
   a base electrical outlet in the base housing configured for electrically coupling the lighting control system with a corded luminaire via a luminaire electrical plug;
   a sensor system coupled to the base housing; and
   a controller communicably coupled to the sensor system, the controller configured to control a flow of electricity received through the base electrical plug from the wall electrical outlet to the corded luminaire via the luminaire electrical plug based on an input detected by a vibration sensor of the sensor system, wherein the vibration sensor is facing in a downward direction.

2. The lighting control system according to claim 1, wherein the sensor system comprises at least one sensor positioned on a bottom surface of the base housing.

3. The lighting control system according to claim 1, wherein the sensor system comprises at least one sensor positioned on a top surface of the base housing.

4. The lighting control system according to claim 1, wherein the corded luminaire is free standing.

5. The lighting control system according to claim 1, wherein sensor system further comprises at least one of a sonar sensor, a low-pass microphone, a RF sensor, a radar, a $CO_2$ sensor, a humidity sensor, or a thermometer.

6. The lighting control system according to claim 1, wherein the base electrical outlet is positioned in a peripheral portion of the base housing.

7. The lighting control system according to claim 1, wherein the controller is configured to determine a floor type from a detection of the vibration sensor.

8. The lighting control system according to claim 1, wherein the base housing is disk shaped.

9. The lighting control system according to claim 1, wherein the controller is configured to auto-tune a strength of the sensor system dependent upon a proximity of the lighting control system to one or more pieces of surrounding furniture and walls detected via one of an ultrasonic or a time-of-flight sensor.

10. The lighting control system according to claim 1, wherein the controller is configured to auto-tune a strength of a wireless antenna dependent upon proximity to surrounding occluding furniture and walls via use of ultrasonic and/or time-of-flight sensors.

11. The lighting control system according to claim 1, wherein the controller is configured to map out a premises floor plan using multiple lighting control systems in unison based on one or more of (1) using a call and response to determine relative distances and/or angles between the multiple lighting control systems, (2) using an RSSI measurement between the multiple lighting control systems, (3) using the multiple lighting control systems as radar sensors or (4) using ultra-sonic speakers and microphones of the multiple lighting control systems to triangulate distances from one or more walls and each other.

12. The lighting control system according to claim 1, wherein the controller is configured to analyze temperature differentials, thermal deficiencies, and an environment profile throughout a premises using temperature and humidity sensors included in a plurality of lighting control systems positioned throughout the premises.

13. The lighting control system according to claim 1, wherein the controller is configured to monitor a biological sleep pattern via a motion sensor and/or microphone.

14. The lighting control system according to claim 1, wherein the controller is configured to analyze changes in occupancy via changes in $CO_2$ readings obtained by the sensor system.

15. The lighting control system according to claim 1, wherein the controller is configured to monitor air quality by measuring particulates and CO levels and at least one of (1) communicate one or more countermeasures wirelessly to an HVAC system, (2) notify a user, (3) send a notification to a mobile electronic device or (4) activate an alarm system.

16. The lighting control system according to claim 1, wherein the controller is configured to communicate to another lighting control system via low-frequency audio through one or more floors and walls in a premises.

17. The lighting control system according to claim 1, wherein the controller is configured to detect a bulb type of a bulb connected to the corded luminaire using at least one of a current sensor or voltage sensor to analyze the flow of electricity received through the base electrical plug.

18. The lighting control system according to claim 1, wherein the controller is configured to turn on the corded luminaire to provide a nightlight in response to sensing vibration.

19. The lighting control system according to claim 1, wherein the controller is configured to turn on the corded luminaire to provide a nightlight in response to sensing vibration and detecting that a room is dark.

20. The lighting control system according to claim 19, wherein the controller is configured to adjust an intensity of the nightlight in response to changes in a strength of the sensed vibration.

21. The lighting control system according to claim 1, wherein the controller is configured to analyze vibration sensed by the vibration sensor concurrently with activating the corded luminaire as a wake up alarm.

22. The lighting control system according to claim 21, wherein the controller is configured to deactivate the alarm once the vibration sensor detects that an occupant has one of stood up or begun walking.

23. The lighting control system according to claim 1, wherein the controller is configured to monitor motion and track behavior of a pet using the sensor system in 360-degrees of direction.

24. The lighting control system according to claim 1, wherein the sensor system further comprises one or more of: a passive infrared sensor, an ultra-sonic sensor, a time-of-flight sensor, a motion/seismic sensor, or a microphone.

25. The lighting control system according to claim 1, where the controller is configured to monitor child movement of a child and deter the child via an alert when the child is determined to be in close proximity to a pre-identified dangerous area.

26. The lighting control system according to claim 1, wherein the controller is configured to guide a pet toward or away from areas of a premises using high-frequency audio.

27. The lighting control system according to claim 26, wherein a loudness of the high frequency audio is greater in spaces to guide away from and quieter in spaces to guide toward as a destination.

28. A lighting control system comprising:

a base housing configured for positioning on a floor surface;

a base electrical plug extending from the base housing and configured for plugging into a wall electrical outlet;

a base electrical outlet in the base housing configured for electrically coupling the lighting control system with a corded luminaire via a luminaire electrical plug;

a sensor system coupled to the base housing; and a controller communicably coupled to the sensor system, the controller configured to control a flow of electricity received through the base electrical plug from the wall electrical outlet to the corded luminaire via the luminaire electrical plug based on an input detected by a vibration sensor of the sensor system, wherein the controller is configured to determine a floor type from a detection of the vibration sensor.

* * * * *